US007026111B2

(12) United States Patent
Clausell et al.

(10) Patent No.: US 7,026,111 B2
(45) Date of Patent: Apr. 11, 2006

(54) METHODS AND REAGENTS FOR IMPROVED CELL-BASED ASSAYS

(75) Inventors: Adrian Clausell, San Diego, CA (US); Jirong Gu, Irvine, CA (US); M. Parameswara Reddy, Brea, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 125 days.

(21) Appl. No.: 09/978,498

(22) Filed: Oct. 15, 2001

(65) Prior Publication Data

US 2003/0077569 A1   Apr. 24, 2003

(51) Int. Cl.
*C12Q 1/00* (2006.01)
(52) U.S. Cl. .................... 435/4; 435/6; 435/11; 435/13; 435/14; 435/18; 435/19; 435/20; 435/21; 435/23; 435/24; 435/219; 435/226; 436/63; 436/64; 436/164; 436/172
(58) Field of Classification Search ................. 435/23, 435/18, 19, 219, 226, 74, 6, 11, 13, 14, 20, 435/21, 24, 4; 436/63, 64, 164, 172
See application file for complete search history.

(56) References Cited

U.S. PATENT DOCUMENTS

| | | | |
|---|---|---|---|
| 4,557,862 A | 12/1985 | Mangel et al. | 260/112 |
| 4,640,893 A | 2/1987 | Mangel et al. | 435/23 |
| 4,940,659 A | 7/1990 | Warrington et al. | 435/7 |
| 5,070,012 A | 12/1991 | Nolan et al. | 435/6 |
| 5,238,108 A | 8/1993 | Velezis et al. | 206/315.1 |
| 5,310,687 A | 5/1994 | Bard et al. | 436/518 |
| 5,698,411 A | 12/1997 | Lucas et al. | 435/29 |
| 5,759,781 A | 6/1998 | Ward et al. | 435/6 |
| 5,976,822 A | 11/1999 | Landrum et al. | 435/23 |
| 6,174,673 B1 | 1/2001 | Short et al. | 435/6 |
| 6,248,904 B1 | 6/2001 | Zhang et al. | 549/227 |
| 6,281,021 B1 | 8/2001 | Egger et al. | 436/544 |

OTHER PUBLICATIONS

Los et al , Nature 375: 81-83, 1995.*
Wansink et al . J. Cell. Biol. 122(2):283-293, 1993.*
Alberts, B. et al., Molecular Biology of the Cell, 2nd Edition. Garland Publishing, Inc. New York, p. 704.
Alnemri, et al., "Human ICE/CED-3 protease nomenclature," *Cell*, 1996 Oct. 18;87(2):171.
Ashmun RA and Look AT. 1990, "Metalloprotease Activity of CD13/Aminopeptidase N on the Surface of Human Myeloid Cells," *Blood* 75: 462-469.
Bass, D.A. et al. "Flow cytometric studies of oxidative product formation by neutrophils: a graded response to membrane stimulation." *J. Immunol*. 130: 1910-1917.
Bode, W. et al., 1989, "Human leukocyte and porcine pancreatic elastase: X-ray crystal structures, mechanism, substrate specificity and mechanism-based inhibitors," *Biochem*. 28: 1951-1963.
Coates, P.M. et al., 1975, "A preliminary genetic interpretation of the esterase isozymes of human tissues," *Ann. Hum. Genet. Lond*. 39: 1-20.
Crockard, A. et al., 1982, "Cytochemistry of acid hydrolases in chronic B-and T-cell leukemias," *Am. J. Clin. Pathol*. 78:437-444.
Darzynkiewicz, Z. et al. "Flow cytometry in analysis of cell cycle and apoptosis," *Semin Hematol*. 2001 (Apr.,38(2):179-93.
Duque, R. E., "Flow Cytometric Analysis of Lymphomas and Acute Leukemias", *Annals of the New York Academy of Sciences, Clinical Flow Cytometry*, 677, pp. 309-325 (Mar. 20, 1993).
Ferrer-Lopez, P. et al., "Heparin Inhibits Neutrophil-Induced Platelet Activation Via Cathepsin",*J. Lab Clin. Med*. 119(3), 231-239 (1992).
Fleischer, B., 1994, "CD26: a surface protease involved in T-cell activation," *Immunol. Today*. 15: 180-184.
Gartner, T.K. et al., 1985, "The tetrapeptide analogue of the alpha chain and decapeptide analogue of the gamma chain of fibrinogen bind to different sites on the platelet fibrinogen receptor," *Blood*. 66 Suppl 1: 305a.
Hoffmann, T. et al. 1993, "Dipeptidyl peptidase IV (CD 26) and aminopeptidase N (CD 13) catalyzed hydrolysis of cytokines and peptides with N-terminal cytokine sequences, " *FEBS Letters*. 336: 61-64.
Hohn, P.A. et al., 1989, "Genomic organization and chromosomal localization of the human cathepsin G gene," *J. Biol. Chem*. 264: 13412-13419.
Jongkind, J.F. et al., 1986, "Detection of acid-b-galactosidase activity in viable human fibroblasts by flow cytometry," *Cytometry* 7:463-466.
Kankaanranta, H. et al., 1994, "Effects of non-steroidal anti-inflammatory drugs on polymorphonuclear leukocyte functions in vitro: focus on fenamates," *Naunyn-Schmiedeberg's Arch Pharmacol*. 350:685-691.
Kohen, E. et al., 1993, "An in situ study of beta-glucosidase activity in normal and gaucher fibroblasts with fluorogenic probes," *Cell Biochem. and Function*. 11:167-177.
Kojima, K. et al., 1979, "A new and highly sensitive fluorescence assay for collagenase-like peptidase activity," *Anal. Biochem*. 100: 43-50.
Leytus, S.P. et al., "New class of sensitive and selective fluorogenic substrates for serine proteases," *Biochem. J*. 215:253-260 (1983).
Li, C.Y. et al., 1970, "Acid phosphatase isoenzyme in human leukocytes in normal and pathologic conditions," *J. Histochem. Cytochem*. 18:473-481.

(Continued)

Primary Examiner—Francisco C. Prats
(74) *Attorney, Agent, or Firm*—Jeffrey I. Auerbach; Berenato, White & Stavish, LLC

(57) ABSTRACT

The ability to efficiently determine the state of enzyme expression in cells has long been desired as material to the diagnosis of disease. This invention relates to cytoenzymology, and more particularly to improved reagents for use in cell-based assays, especially those using fluorogenic substrates.

44 Claims, 11 Drawing Sheets

OTHER PUBLICATIONS

Look, A.T. et al. 1989, "Human myeloid plasma membrane glycoprotein CD13 (gp150) is identical to aminopeptidase N,"*J. Clin. Invest.* 83: 1299-1307.

McDonald, J.A. et al., 1980, "Degradation of fibronectin by human leukocyte elastase," *J. Biol. Chem.* 255: 8848-8858.

Mentlein, R. et al., H. R., "Influence of Pregnancy on Dipeptidyl Peptidase IV Activity (CD26 Leukocyte Differentiation Antigen) of Circulating Lymphocytes", *Eur. J. Clin. Chem. Clin. Biochem.*, 29, 477-480 (1991).

Mononen, et al., "Enzymatic diagnosis of aspartylglycosaminuria by fluorometric assay of glycosylasparaginase in serum, plasma, or lymphocytes," *Clin. Chem.* 1994 Mar.; 40(3):385-8.

Park, R.D. et al., "Hypertonic sucrose inhibition of endocytic transport suggests multiple early endocytic compartments," *J. Cell Physiol.* 1988 Jun.;135(3):443-450).

Rechsteiner, M. "Osmotic lysis of pinosomes," Methods Enzymol 1987;149:42-48; Okada, C.Y. et al., "Introduction of macromolecules into cultured mammalian cells by osmotic lysis of pinocytic vesicles," *Cell* 1982 May;29(1): 33-41.

Riss, T.L. "Apoptosis as a biomarker in chemoprevention trials," *Urology*. 2001 Apr.;57(4 suppl 1):141-2.

Rothe et al., "Flow cytometric analysis of protease activities in vital cells,"*Biol. Chem. Hoppe Seyler*. Jul. 1992; 373(7): 547-54.

Rotman, B. et al., 1963, "Fluorogenic substrates for b-D-galactosidases and phosphatases derived from fluorescein (3,6-dihydroxyfluoran) and its monomethyl ether," *Proc. Nat. Acad. Sci.* USA 50:1-6.

Royer, G. et al., "Immobilized Derivatives of Leucine Aminopeptidase and Aminopeptidase M," *J. Biol. Chem.* 248(5), 1807-1812 (1973).

Ruiz, P. et al., 1996, "Cytofluorographic evidence that-thymocyte dipeptidyl peptidase IV (CD26) activity is altered with stage of ontogeny and apoptotic status," *Cytometry*. 23: 322-329.

Sanderink, G.J. et al., 1988, Human Aminopeptidases: A Review of the Literature. *J. Clin. Chem. Clin. Biochem.* 26: 795-807.

Saraste, A. et al. "Morphologic and biochemical hallmarks of apoptosis," *Cardiovasc Res.* 2000 Feb.;45(3):528-37.

Saraste, A. et al. "Morphologic criteria and detection of apoptosis," *Herz*. May 1999;24(3):189-95.

Schon, E. et al., "The role of dipeptidyl peptidase IV in human T lymphocyte activation. Inhibitors and antibodies against dipeptidyl peptidase IV suppress lymphocyte proliferation and immunoglobulin synthesis in vitro," *Eur. J. Immunol*. Dec. 1987;17(12):1821-6.

Stein, R.L. et al. 1987, "Catalysis by human leukocyte elastase: Mechanistic insights into specificity requirements," *Biochem.* 26:1301-1305.

Stein, R.L. et al. 1987, "Catalysis by human leukocyte elastase: Proton inventory as a mechanistic probe," *Biochem.* 26:1305-1314.

Tanaka, T. et al., 1993, "The costimulatory activity of the CD26 antigen requires dipeptidyl peptidase IV enzymatic activity," *Proc. Natl. Acad. Sci.* USA. 90: 4586-4590.

Thiele, D.L. et al., 1990, "Mechanism of L-leucyl-L-leucine methyl ester-mediated killing of cytotoxic lymphocytes: Dependence on a lysosomal thiol protease, dipeptidyl peptidase I, that is enriched in these cells," *Proc. Natl. Acad. Sci. USA*. 87:83-87.

Valet et al, "White cell and thrombocyte disorders. Standardized, self-learning flow cytometric list mode data classification with the CLASSIF1 program system," *Ann. NY Acad. Sci*. Mar. 20, 1993;677-233-51.

Watson, J., "Enzyme Kinetic Studies in Cell Population Using Fluorogenic Substrates and Flow Cytometric Techniques," *Cytometry*, 1(2), p. 143 (1980).

Weiss. S.J. 1989, "Tissue destruction by neutrophils," *N. Eng. J. Med.* 320: 365-376.

Whitlock, C.A., et al., 1987. "Bone marrow stromal cell lines with lymphopoietic activity express high levels of a pre-B neoplasia-associated molecule," *Cell* 48:1009-1021.

Woessner, J.F. Jr., 1991, "Matrix metalloproteinases and their inhibitors in connective tissue remodeling," *FASEB J.* 5: 2145-2154.

Wu, Q. et al., 1991. "Aminopeptidase A activity of the murine B-lymphocyte differentiation antigen BP-1/6C3," *Proc. Natl. Acad. Sci*, USA. 88: 676-680.

Kirby, C.J. et al. (1977) "Cholesterol Uptake by Erythrocyte Membranes," Biochem. Soc. Trans. 5(4): 1160-1162.

1978:16553 CAPLUS (Abstracted from Kirby, C.J. et al. (1977) "Cholesterol Uptake by Erythrocyte Membranes," Biochem. Soc. Trans. 5(4): 1160-1162).

* cited by examiner

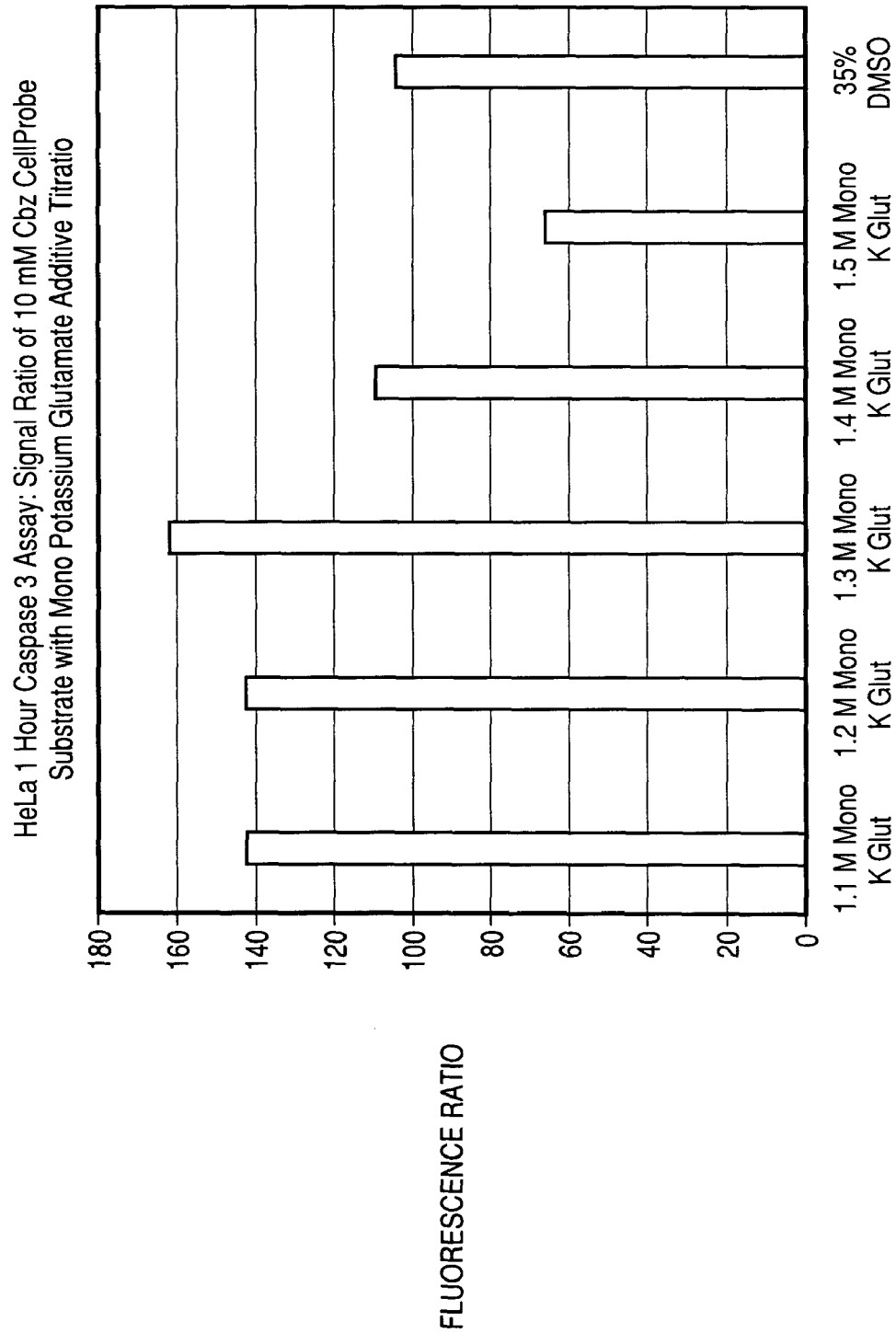

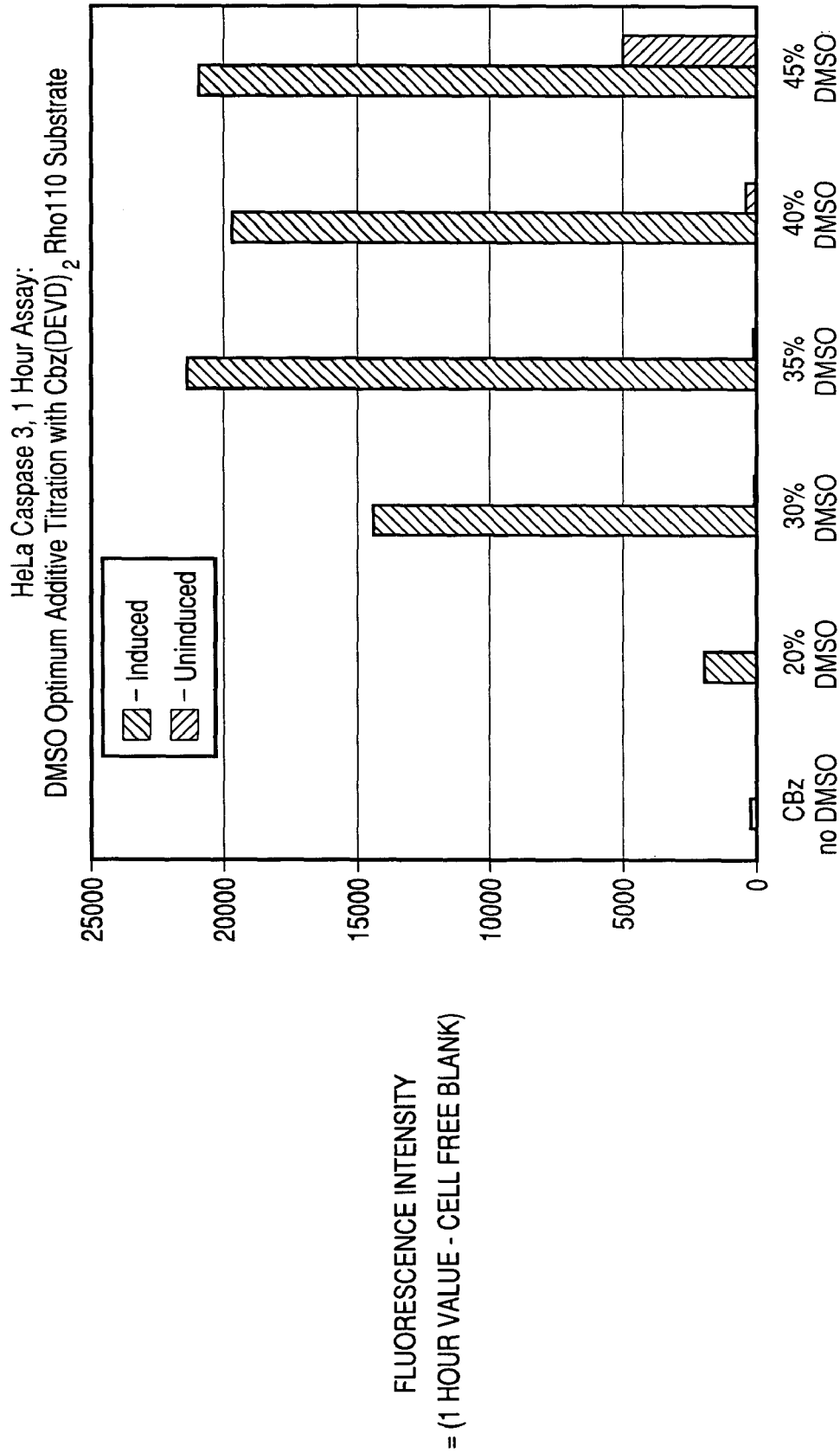

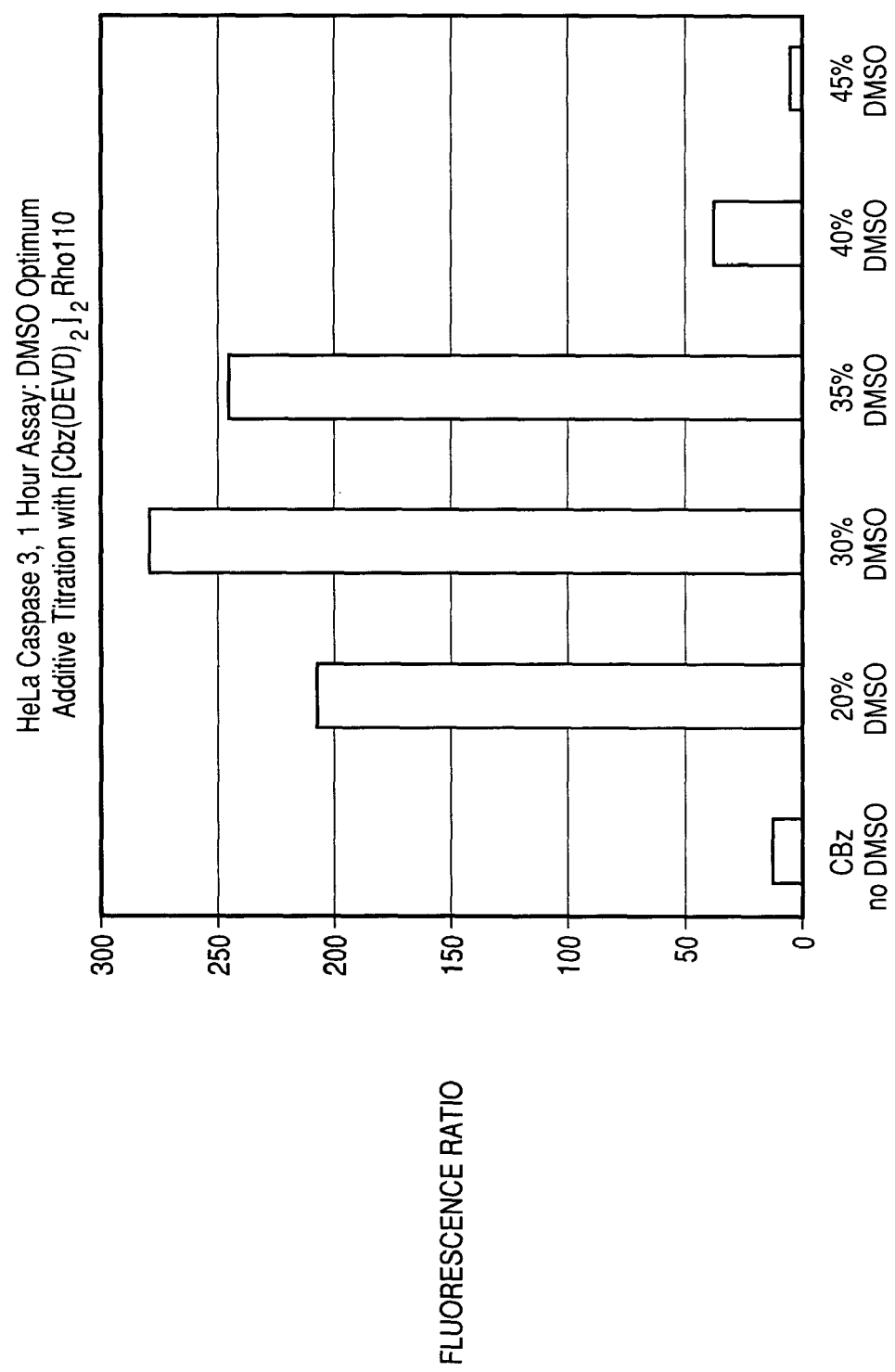

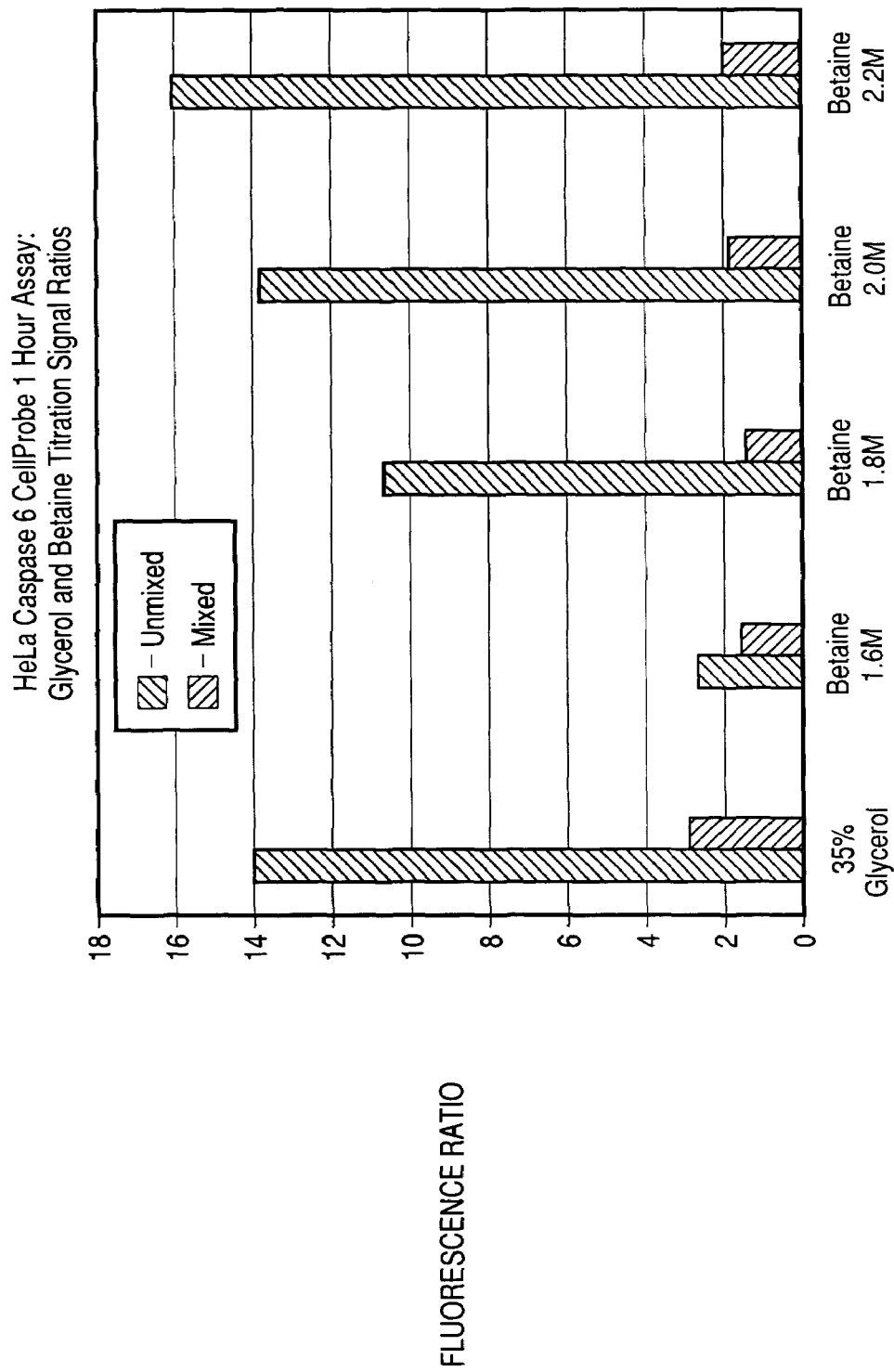

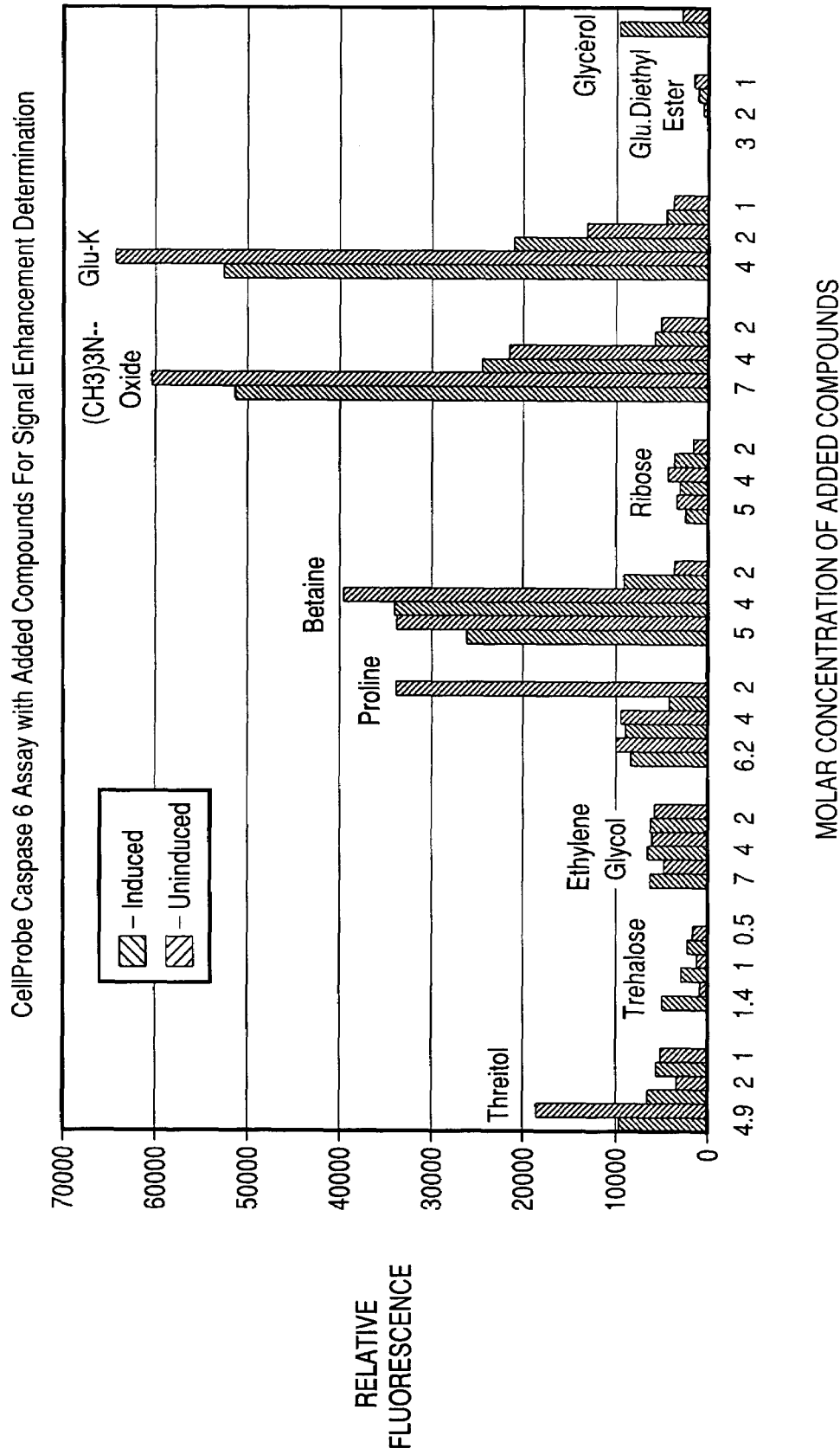

METHODS AND REAGENTS FOR IMPROVED CELL-BASED ASSAYS

FIELD OF THE INVENTION

This invention relates to cytoenzymology, and more particularly to methods and improved reagents for use in cell-based assays, especially those using fluorogenic substrates.

BACKGROUND OF THE INVENTION

Cytoenzymology is the study of enzymes as they function on and within cells. Dead or metabolically inactive cells can have as little as approximately one-quarter the enzymatic activity of living cells, Watson, J., "Enzyme Kinetic Studies in Cell Population Using Fluorogenic Substrates and Flow Cytometric Techniques", Cytometry, 1(2), p. 143 (1980). Further, because enzymes are frequently bound in highly organized enzyme pathways, the activity of enzymes can reveal cell disruption or death.

Previously, the study of enzymatic activity within cells has been pursued primarily by three methods. The first such method determines enzyme activity by studying extra-cellular events, such as the presence or lack of the products of enzyme activity (see. e.g., Warrington, et al., U.S. Pat. No. 4,940,659; Short, et al., U.S. Pat. No. 6,174,673, etc.).

In the second such method, the cell membrane is ruptured in order to create a cytosol of cellular components including the enzyme that is the object of study. Various tests may then be performed, using either the cytosol or the purified enzyme in order to determine the activity of the enzyme. One such approach involves incubating the cell in culture medium containing high concentrations of sucrose or polyethylene glycol in order to break cellular membranes and release cytosol (Rechsteiner, M. "Osmotic lysis of pinosomes," Methods Enzymol 1987;149:42–48; Okada, C. Y. et al., "Introduction of macromolecules into cultured mammalian cells by osmotic lysis of pinocytic vesicles," Cell 1982 May;29(1):33–41; Park, R. D. et al., "Hypertonic sucrose inhibition of endocytic transport suggests multiple early endocytic compartments," J Cell Physiol 1988 June;135(3): 443–450). A second such test is to provide a substrate, that is recognized by the enzyme, with a fluorescent compound which will undergo a detectable change when the substrate, or "leaving group", is cleaved from the compound by the enzyme (see, for example Mangel et al., U.S. Pat. Nos. 4,557,862 and 4,640,893, which disclose rhodamine 110-based derivatives as fluorogenic substrates for proteinases). G. Rothe et al., *Biol. Chem. Hoppe-Seyler,* 373, 544–547 (1992) describe the analysis of proteinase activities using the substituted peptide-rhodamine 110 derivatives of Mangel et al. Moreover, G. Valet et al, *Ann NY Acad Sci,* 667, 233–251 (1993), disclose the study of white cell and thrombocyte disorders with the rhodamine 110 derivatives of Mangel et al. The methods of Rothe and Valet have been used to conduct cytoenzymological studies on the activity of enzymes with cells, but the compounds utilized by Rothe and Valet are not suitable for the study of the activity of intracellular enzymes in vital cells. The Mangel et al. compounds cannot be efficiently solubilized and transmitted through the cell membrane in a manner which will produce a reliable assay. I. Mononen, et al., Clin. Chem., 40(3), 385–388 (1994), describe the enzymatic diagnosis of aspartylglycos-aminuria by the fluorometric assay of glycosylasparaginase in serum, plasma, and lymphocytes. The study was conducted on cytosols, and not whole cells, and utilized an asparagine-substituted 7-amino-4-methylcoumarin. U.S. Pat. No. 5,070,012 to Nolan et al., describes a method of monitoring cells and trans-acting transcription elements. This method, however, is not designed for the monitoring of enzymes which are endogenous to the cell being tested.

Lucas, et al. (U.S. Pat. No. 5,698,411) and Landrum et al. (U.S. Pat. No. 5,976,822) describe the third general method for assaying enzyme activity. In this method, the enzyme activity of metabolically active whole cell s is determined. The assay employs reagents that comprise at least one water soluble assay compound having the ability to pass through a cell membrane or a water soluble physiologically acceptable salt thereof having the ability to pass through a cell membrane. The assay compound has (i) a leaving group selected so that it may be cleaved by an enzyme to be analyzed and (ii) a fluorogenic indicator group selected for its ability to have a non-fluorescent first state when joined to the leaving group, and a fluorescent second state excitable at a convenient wavelength (e.g., a wavelength above 450 nm) when the leaving group is cleaved from the indicator group by the enzyme.

Landrum et al. (U.S. Pat. No. 5,976,822) discloses assay reagents for determining the activity of an enzyme in a metabolically active whole cell, in which the assay reagent comprises at least one water soluble physiologically acceptable salt having the ability to pass through a cell membrane. The assay compound has an unblocked leaving group selected for cleavage by an enzyme to be analyzed (such as a cysteine protease (especially a caspase enzyme or a granzyme of cysteine proteases), dipeptyl peptidase and calpain), and a fluorogenic indicator group selected for its ability to have a non-fluorescent first state when joined to the leaving group, and a fluorescent second state excitable at a wavelength when the unblocked leaving group is cleaved from the indicator group by the enzyme. Various indicator groups are disclosed (4'(5')aminorhodamine 110, 4'(5')carboxyrhodamine 110, 4'(5')chlororhodamine 110, 4'(5')methylrhodamine 110, 4'(5')sulforhodamine 110, 4'(5')aminorhodol, 4'(5')carboxyrhodol, 4'(5')chlororhodol, 4'(5') methylrhodol, 4'(5')sulforhodol, 4'(5')aminofluorescein, 4'(5')carboxyfluorescein, 4'(5')chlorofluorescein, 4'(5')methylfluorescein, and 4'(5')sulfofluorescein).

Such enzyme assays are particularly desirable for determining the activity of enzymes associated with tumor cell progression or apoptosis. Apoptosis, or programmed cell death, is a process that involves the activation of a genetic program when cells are no longer needed or have become seriously damaged. This process, occurring in most cells from higher eukaryotes, is necessary for normal development and maintenance of homeostasis. It is a major defense mechanism of the body, permitting the body to eliminate unwanted and possibly dangerous cells such as virus-infected cells, tumor cells, and self-reactive lymphocytes.

Apoptosis involves a cascade of specific biochemical events, and its regulation involves a large number of enzymes. These can be classified into three general categories. The first is made up of enzymes whose primary function is to suppress apoptosis. This group includes some members of the bcl-2 family. Other members of the bcl-2 family can promote apoptosis. The second group includes the intermediate genes upstream such as Fas/Fas ligand, myc, p53, and WAF1. Fas is a cell surface protein that triggers apoptosis in a variety of cell types. The Fas death pathway can be triggered by either anti-Fas monoclonal antibody or by cell-associated Fas ligand. This protein is identical to the CD95 protein. CD95 is involved in regulation of tissue development and homeostasis. Cloning of Fas and APO-1 cDNA has demonstrated that these two genes are identical. The Fas antigen is a cell surface protein that belongs to the tumor necrosis factor/nerve growth factor receptor family.

The last group includes genes, such as cysteine proteases that act as effectors of apoptosis. An example is the interleukin-1β converting enzyme (ICE) family of genes. Several homologues of ICE have been identified, including CPP32- and Ich-1-like proteases. Specific inhibitors of ICE-like proteases can inhibit apoptosis. This indicates there is a requirement for specific degradation by proteases in mammalian apoptosis. The ICE family of cysteine proteases has an indispensable role in the regulation of apoptosis. It appears that the ICE family of proteases process themselves and each other by proteolytically cleaving a "pre" enzyme into the active form. The ICE family of proteases is generically referred to as "caspase" enzymes (Alnemri, et al., *Cell*, Volume 87, page 171, 1996. Caspases are also thought to be crucial in the development and treatment of cancer. The "c" is intended to reflect a cysteine protease mechanism and "aspase" refers to their ability to cleave after aspartic acid, the most distinctive catalytic feature of this protease family).

Caspase proteases are reviewed by Darzynkiewicz, Z. et al. ("Flow cytometry in analysis of cell cycle and apoptosis," *Semin Hematol.* 2001 April;38(2):179–93); Riss, T. L. ("Apoptosis as a biomarker in chemoprevention trials," *Urology.* 2001 April;57(4 Suppl 1):141–2); Saraste, A. et al. ("Morphologic and biochemical hallmarks of apoptosis," *Cardiovasc Res.* 2000 February;45(3):528–37); Akao, Y. et al. ("Arsenic-induced apoptosis in malignant cells in vitro," Leuk Lymphoma. 2000 March;37(1–2):53–63); Bannerman, D. D. et al. ("Direct effects of endotoxin on the endothelium: barrier function and injury," Lab Invest. 1999 October;79 (10):1181–99); Saraste, A. et al. ("Morphologic criteria and detection of apoptosis," *Herz.* 1999 May;24(3):189–95); Levy-Strumpf, N. et al. ("Death associated proteins (DAPs): from gene identification to the analysis of their apoptotic and tumor suppressive functions," *Oncogene.* 1998 December 24;17(25):3331–40); Warner, C. M. et al. ("Role of the Ped gene and apoptosis genes in control of preimplantation development," *J Assist Reprod Genet.* 1998 May;15(5): 331–7); Tocci, M. J. ("Structure and function of interleukin-1 beta converting enzyme," *Vitam Horm.* 1997;53:27–63); Miller, D. K. et al. ("The IL-1 beta converting enzyme as a therapeutic target," *Ann NY Acad Sci.* 1993 Nov. 30;696:133–48). Zhang, et al. (U.S. Pat. No. 6,248,904) discusses fluorescence dyes and their applications for whole-cell fluorescence screening assays for caspases, peptidases, proteases and other enzymes and the use thereof Despite all such advances, a need exists for improved reagents for use in cytoenzymology, and particularly for improved reagents that can be used to assay enzymes associated with tumor cell progression or apoptosis. The present invention addresses such a need.

SUMMARY OF THE INVENTION

This invention relates to improved reagents for cell-based assays using fluorogenic substrates. The invention further relates to improved assays using such reagents.

In detail, the invention concerns a method for enhancing the uptake of a molecule into a metabolically active whole cell, comprising incubating said metabolically active whole cell with said molecule in the presence of an agent that causes increased uptake of molecules into metabolically active cells, said agent being present at a concentration sufficient to enhance the uptake of said substrate or analyte compound into said metabolically active whole cell. The invention particularly concerns the embodiment of such method wherein the agent that causes such increased uptake of molecules into metabolically active cells is selected from the group consisting of glycerol, dimethyl sulfoxide (DMSO), trehalose, glutamate, betaine, ethylene glycol, threitol, ribose, and trimethylamine N-oxide. The invention additionally concerns the embodiment of such methods wherein the molecule that is taken up be the cell permits the staining, imaging or visualization of the cell or of structures, regions or molecules within the cell. The invention further concerns the embodiment of such methods wherein such molecule is selected from the group consisting of a lectin, a nucleic acid, a paramagnetic moiety, an enzyme substrate or an analyte.

The invention additionally concerns a method for assaying for the presence or activity of an enzyme in a metabolically active whole cell, comprising the steps:
(a) incubating the metabolically active whole cell with a substrate of the enzyme or an analyte compound in the presence of an agent that enhances uptake of the substrate or analyte, the agent being present at a concentration sufficient to enhance the uptake of the substrate or analyte compound;
(b) assaying for any change in concentration of the substrate or analyte compound or of a product formed via action of the enzyme on the substrate or analyte;
   wherein a change in the concentration is indicative of the presence or activity of the enzyme in the metabolically active whole cell.

The invention additionally concerns the embodiments of such methods wherein the substrate or analyte compound comprises comprising an indicator group (especially a fluorescent, colorimetric, paramagnetic, bioluminescent or chemiluminescent indicator group) and one or more leaving groups, each of the leaving groups being selected for cleavage by the enzyme, the indicator group being in a first state when bonded to a leaving group, and being in a second state when the leaving group is cleaved from the indicator group by the enzyme; and wherein the step (b) comprises sensing whether the second state of the indicator group is produced; wherein the production of the second state of the indicator group is indicative of the presence or activity of the enzyme in the metabolically active whole cell.

The invention additionally concerns the embodiments of such methods wherein the substrate or analyte compound comprises more than one leaving group, and wherein each of the substrate's leaving groups is cleaved consecutively by the enzyme to ultimately yield a free dye.

The invention additionally concerns the embodiments of such methods wherein the indicator group is selected from the group consisting of rhodamine 110, rhodol, fluorescein, coumarin, and derivatives thereof (especially wherein the derivatives of rhodamine 110, rhodol, fluorescein and coumarin are selected from the group consisting of 4'(5')thiofluorescein, 4'(5')-aminofluorescein, 4'(5')-carboxyfluorescein, 4'(5')-chlorofluorescein, 4'(5')-methylfluorescein, 4'(5')-sulfofluorescein, 4'(5')-aminorhodol, 4'(5')-carboxyrhodol, 4'(5')-chlororhodol, 4'(5')-methylrhodol, 4'(5')-sulforhodol; 4'(5')-aminorhodamine 110, 4'(5')-sulforhodamine 110, 4'(5')thiorhodamine 110, 7-aminocoumarin, and sulfonated coumarin).

The invention additionally concerns the embodiments of such methods wherein the substrate or analyte compound contains a blocking group (for example a Cbz blocking group).

The invention additionally concerns the embodiment of such methods wherein the enzyme is selected from the group consisting of a 5' nucleotidase, acetylcholinesterase, an acid phosphatase, an acidic esterase, an acidic esterase I, an acidic esterase II, an acidic non-specific esterase, an adenosine deaminase, an adenosine monophosphate deaminase, an alkaline phosphatase, an aminopeptidase A, an aminopeptidase B, an aminopeptidase M, an Aminopeptidase N, an angiotensin converting enzyme, a caspase, a cathepsin B, a cathepsin B1, a cathepsin C, a cathepsin D, a cathepsin H, a cathepsin L, a cholinesterase, a cholinesterase, a chymotrypsin, a collagenase, a cytosine deaminase, a DPP I, a DPP II, a DPP IV, an elastase, an endopeptidase I, an endopeptidase II, an ester proteinase, a galactopyranosidase, a glucoronidase, a glutathione, a glycopyranossidase, a guanine deaminase, an HIV Protease, a lipase, a membrane associated endopeptidase I, a membrane associated endopeptidase II, a neutral endopeptidase, a neutral esterase, a neutral esterase I, a neutral esterase II, a neutral non-specific esterase, a nucleosidase, a pancreatin, a phospholipase A, a phospholipase C, a phospholipase D, a plasmin, a serine phosphatase, a tartrate resistant phosphatase, a tartrate resistant phosphatase, a threonine phosphatase, a thymidine deaminase, a tripeptidyl peptidase, a trypsin, a tyrosine phosphatase, a urokinase, a v-thrompsin, and a γ-GT.

The invention additionally concerns the embodiments of such methods wherein the substrate or analyte compound of the enzyme and the uptake-enhancing agent are mixed during the incubation, and wherein the substrate or analyte compound of the enzyme and the uptake-enhancing agent are not mixed during the incubation.

The invention additionally concerns the embodiments of such methods wherein multiple enzymes are simultaneously assayed and wherein multiple enzymes are sequentially assayed.

The invention additionally concerns the embodiments of such methods wherein the uptake-enhancing agent is selected from the group consisting of glycerol (especially wherein the glycerol concentration is between about 5% and about 60% (v/v), or between about 20% and about 60% (v/v) or between about 25% and about 40% (v/v)), dimethyl sulfoxide (DMSO) (especially wherein the DMSO concentration is between about 5% and about 60% (v/v), or between about 20% and about 60% (v/v)), trehalose (especially wherein the trehalose concentration is between about 0.1 M and about 1.5 M), glutamate (especially wherein the glutamate concentration is between about 0.25 M and about 2.0 M, or between about 1 M and about 2 M), betaine (especially wherein the betaine concentration is about 0.3 M or greater), ethylene glycol (especially wherein the ethylene glycol concentration is between about 2 M and about 7 M), threitol (especially wherein the threitol concentration is between about 1 M and about 5 M), ribose threitol (especially wherein the ribose concentration is between about 0.4 M and about 4 M), and trimethylamine N-oxide (especially wherein the trimethylamine N-oxide concentration is between about 0.4 M and about 4 M).

The invention additionally concerns the embodiments of such methods wherein the step (b) includes measuring an intensity of the second state against time and/or wherein the step (b) includes measuring a magnitude of the second state at a point of time.

The invention additionally concerns the embodiments of such methods wherein the assay detects the presence or absence of an abnormality (especially a morphological state (such as an apoptotic state) or a disease state (such as a tumorigenic state)) in the activity of the enzyme by comparing the production of the second state of the indicator group by the test cell to the production of the second state of the indicator group by a reference normal cell.

The invention further concerns a reagent for assaying the activity of an enzyme comprising a substrate or analyte compound of the enzyme and an uptake-enhancing agent, the agent being present at a concentration sufficient to enhance the uptake of the substrate or analyte compound in a metabolically active cell.

The invention further concerns the embodiments of such reagent wherein the enzyme is selected from the group consisting of a 5' nucleotidase, acetylcholinesterase, an acid phosphatase, an acidic esterase, an acidic esterase I, an acidic esterase II, an acidic non-specific esterase, an adenosine deaminase, an adenosine monophosphate deaminase, an alkaline phosphatase, an aminopeptidase A, an aminopeptidase B, an aminopeptidase M, an Aminopeptidase N, an angiotensin converting enzyme, a caspase, a cathepsin B, a cathepsin B1, a cathepsin C, a cathepsin D, a cathepsin H, a cathepsin L, a cholinesterase, a cholinesterase, a chymotrypsin, a collagenase, a cytosine deaminase, a DPP I, a DPP II, a DPP IV, an elastase, an endopeptidase I, an endopeptidase II, an ester proteinase, a galactopyranosidase, a glucoronidase, a glutathione, a glycopyranossidase, a guanine deaminase, an HIV Protease, a lipase, a membrane associated endopeptidase I, a membrane associated endopeptidase II, a neutral endopeptidase, a neutral esterase, a neutral esterase I, a neutral esterase H, a neutral non-specific esterase, a nucleosidase, a pancreatin, a phospholipase A, a phospholipase C, a phospholipase D, a plasmin, a serine phosphatase, a tartrate resistant phosphatase, a tartrate resistant phosphatase, a threonine phosphatase, a thymidine deaminase, a tripeptidyl peptidase, a trypsin, a tyrosine phosphatase, a urokinase, a v-thrompsin, and a γ-GT.

The invention further concerns the embodiments of such reagent wherein the substrate or analyte compound comprises comprising an indicator group and one or more leaving groups, each of the leaving groups being selected for cleavage by the enzyme, the indicator group being in a first state when bonded to a leaving group, and being in a second state when the leaving group is cleaved from the indicator group by the enzyme; and wherein the step (b) comprises sensing whether the second state of the indicator group is produced; wherein the production of the second state of the indicator group is indicative of the presence or activity of the enzyme in the metabolically active whole cell.

The invention further concerns the embodiments of such reagent wherein the indicator group is a fluorescent, colorimetric, bioluminescent or chemiluminescent indicator group.

The invention further concerns the embodiments of such reagent wherein the uptake-enhancing agent is selected from the group consisting of glycerol (especially wherein the glycerol concentration is between about 5% and about 60% (v/v), or between about 20% and about 60% (v/v) or between about 25% and about 40% (v/v)), dimethyl sulfoxide (DMSO) (especially wherein the DMSO concentration is between about 5% and about 60% (v/v), or between about 20% and about 60% (v/v)), trehalose (especially wherein the trehalose concentration is between about 0.1 M and about 1.5 M), glutamate (especially wherein the glutamate concentration is between about 0.25 M and about 2.0 M, or between about 1 M and about 2 M), betaine (especially wherein the betaine concentration is about 0.3 M or greater), ethylene glycol (especially wherein the ethylene glycol concentration is between about 2 M and about 7 M), threitol (especially wherein the threitol concentration is between about 1 M and about 5 M), ribose (especially wherein the ribose concentration is between about 0.4 M and about 4 M), and trimethylamine N-oxide (especially wherein the trimethylamine N-oxide concentration is between about 0.4 M and about 4 M).

The invention further concerns the embodiments of such reagent wherein the enzyme is selected from the group consisting of a 5' nucleotidase, acetylcholinesterase, an acid phosphatase, an acidic esterase, an acidic esterase I, an acidic esterase II, an acidic non-specific esterase, an adenosine deaminase, an adenosine monophosphate deaminase, an alkaline phosphatase, an aminopeptidase A, an aminopeptidase B, an aminopeptidase M, an Aminopeptidase N, an angiotensin converting enzyme, a caspase, a cathepsin B, a cathepsin B1, a cathepsin C, a cathepsin D, a cathepsin H, a cathepsin L, a cholinesterase, a cholinesterase, a chymotrypsin, a collagenase, a cytosine deaminase, a DPP I, a DPP II, a DPP IV, an elastase, an endopeptidase I, an endopeptidase II, an ester proteinase, a galactopyranosidase, a glucoronidase, a glutathione, a glycopyranossidase, a guanine deaminase, an HIV Protease, a lipase, a membrane associated endopeptidase I, a membrane associated endopeptidase II, a neutral endopeptidase, a neutral esterase, a neutral esterase I, a neutral esterase II, a neutral non-specific esterase, a nucleosidase, a pancreatin, a phospholipase A, a phospholipase C, a phospholipase D, a plasmin, a serine phosphatase, a tartrate resistant phosphatase, a tartrate resistant phosphatase, a threonine phosphatase, a thymidine deaminase, a tripeptidyl peptidase, a trypsin, a tyrosine phosphatase, a urokinase, a v-thrompsin, and a γ-GT.

The invention further concerns the embodiments of such reagent wherein the substrate or analyte compound comprises more than one leaving group, and wherein each of the substrate's leaving groups is cleaved sequentially.

The invention further concerns the embodiments of such reagent wherein the indicator group is selected from the group consisting of rhodamnine 110, rhodol, fluorescein, coumarin, and derivatives thereof (especially wherein the derivatives of rhodamine 110, rhodol, fluorescein and coumarin are selected from the group consisting of 4'(5')thiofluorescein, 4'(5')-aminofluorescein, 4'(5')-carboxyfluorescein, 4'(5')-chlorofluorescein, 4'(5')-methylfluorescein, 4'(5')-sulfofluorescein, 4'(5')-aminorhodol, 4'(5')-carboxyrhodol, 4'(5')-chlororhodol, 4'(5')-methylrhodol, 4'(5')-sulforhodol; 4'(5')-aminorhodamine 110, 4'(5')-sulforhodamine 110, 4'(5')thiorhodamine 110, 7-aminocoumarin, and sulfonated coumarin).

The invention further concerns the embodiments of such reagent wherein the assay detects the presence or absence of an abnormality in the activity of the enzyme by comparing the production of the second state of the indicator group by the test cell to the production of the second state of the indicator group by a reference normal cell.

The invention further concerns the embodiments of such reagent wherein the abnormality is a morphological state (such as an apoptotic state) or a disease state (such as a tumorigenic state)).

The invention further concerns the embodiments of such reagent wherein the substrate or analyte compound contains a blocking group (for example, a Cbz blocking group.

BRIEF DESCRIPTION OF THE FIGURE

FIGS. 6A–6C demonstrate the improved sensitivity of the assays of the present invention resulting from the use of CbZ-blocked cellprobe reagents.

FIG. 7 demonstrates the enhanced detection sensitivity of the assays of the present invention in the presence of betaine.

FIG. 9 demonstrates the enhanced detection sensitivity of the assays of the present invention in the presence of threitol, trehalose, ethylene glycol, proline, ribose, or trimethylamine N-oxide.

DESCRIPTION OF THE PREFERRED EMBODIMENTS

Figure 1:
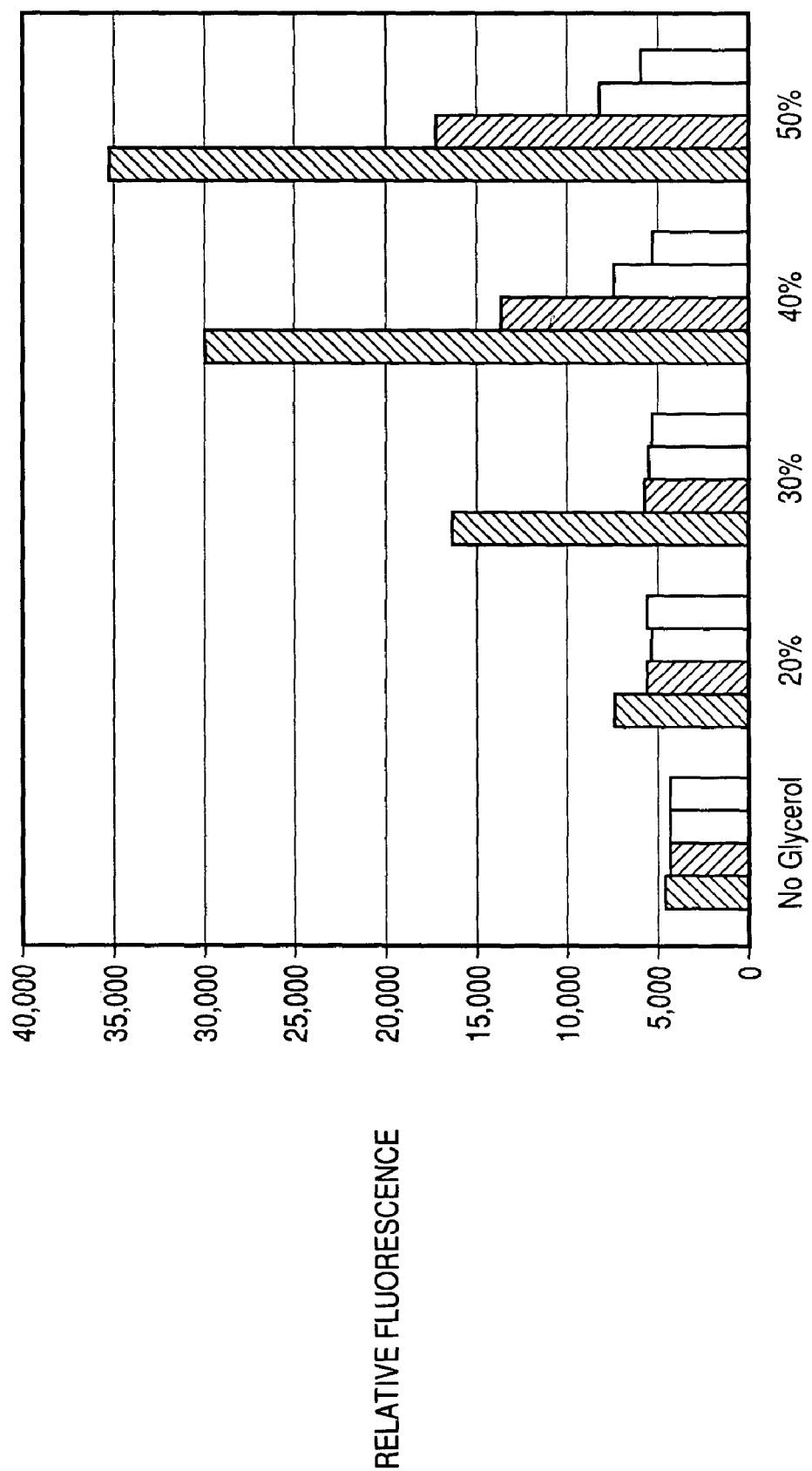
FIG. 1 shows the effect of glycerol on a Caspase 3 CellProbe™ assay with U-937 suspension cells.

The ability to efficiently determine the state or stage of cells has long been desired as a material to the diagnosis of disease. In particular, the use of live, metabolically active cells can yield information to help identify responses unobservable in disrupted cellular extracts.

I. Use of Agents Causing Increased Uptake of Compounds to Improve Cell-Based Assays The present invention extends cell-based assays and investigations to permit the use of a variety of detection and analysis technologies (such as fluorescence, luminescence, bioluminescence, chemiluminescence, pH, ion or analyte concentration, colorimetry, etc.) in the evaluation and/or characterization of cells, especially metabolically active cells. Such extension is mediated by including agents that cause the increased uptake of analytes and/or substrates that are being used to assay cellular function or activity. Without in any way intending to define the mechanism of action of the agents of the present invention, such agents include those that induce hyperosmotic shock, and have the general characteristic of being able to help stabilize or fold proteins and/or assist organisms that experience osmotic shock or need to stabilize themselves from osmotic shock. Such agents include glycerol, dimethyl sulfoxide (DMSO), trehalose, glutamate, betaine, ethylene glycol, threitol, ribose, trimethylamine N-oxide, etc. In one aspect of the present invention, the use of such agents has been found to result in increased uptake and/or transport of substrates and analytes. Such increased uptake and/or transport thus enhances the sensitivity of substrate or analyte detection, and results in improved assays.

Any of a wide variety of enzymes, proteins, etc. may be analyzed in accordance with the principles of the present invention. In particular, the activity or presence of cellular enzymes, including proteases, glycosidases, glucosidases, carbohydrases, phosphodiesterases, phosphatases, sulfatases, thioesterases, pyrophosphatases, lipases, esterases, nucleotidases and nucleosidases may be analyzed. As used herein, the term "carbohydrase" includes any enzyme that has the ability to hydrolyze a carbohydrate. Enzymes which do not recognize and cleave a leaving group, such as dehydrogenases and kinases, are not preferred for assays according to the invention. The enzymes to be measured can be those that are present in various cell preparations, enzymes found in cytosols, cell surface enzymes, cytoplasmic enzymes and cell nucleus (nuclear) enzymes. However, as will be discussed herein, the principles of the present invention are particularly useful for detecting or analyzing intracellular enzymes in living cells. Additional enzymes whose activity or presence may be measured in accordance with the present invention include: 5' nucleotidase, acetylcholinesterase, acid phosphatase, acidic esterase, acidic esterase I, acidic esterase II, acidic non-specific esterase, adenosine deaminase, adenosine monophosphate deaminase, alkaline phosphatase, aminopeptidase A, aminopeptidase B, aminopeptidase M, Aminopeptidase N, angiotensin converting enzyme, caspase (including caspases 1, 3, 6, 8, or 9), cathepsin B, cathepsin B1, cathepsin C, cathepsin D, cathepsin H, cathepsin L, cholinesterase, cholinesterase, chymotrypsin, collagenase, cytosine deaminase, DPP I, DPP II, DPP IV, elastase, endopeptidase I, endopeptidase II, ester proteinase, galactopyranosidase, glucoronidase, glutathione, glycopyranossidase, guanine deaminase, HIV Protease, lipase, membrane associated endopeptidase I, membrane associated endopeptidase II, neutral endopeptidase, neutral esterase, neutral esterase I, neutral esterase II, neutral non-specific esterase, nucleosidase, pancreatin, phospholipase A, phospholipase C, phospholipase D, plasmin, serine phosphatase, tartrate resistant phosphatase, tartrate resistant phosphatase, threonine phosphatase, thymidine deaminase, tripeptidyl peptidase, trypsin, tyrosine phosphatase, urokinase, v-thrompsin, and γ-GT.

Likewise any of a wide variety of analytes and substrates may be used in accordance with the principles of the present invention. In one embodiment, such substrates may contain a fluorescent moiety (including rhodamine 110; rhodol; coumarin or a fluorescein compound):

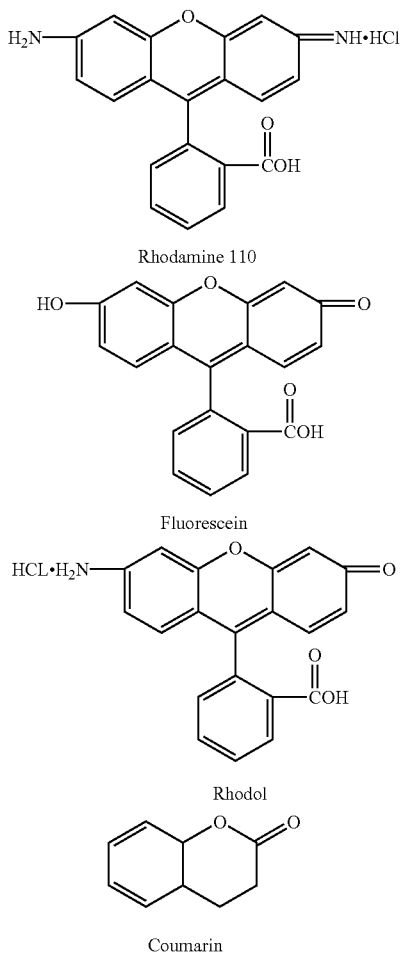

Rhodamine 110

Fluorescein

Rhodol

Coumarin

In addition, derivatives of rhodamine 110, rhodol, or fluorescein compounds that have a 4' or 5' protected carbon may be employed. Preferred examples of such compounds include 4'(5')thiofluorescein, 4'(5')-aminofluorescein, 4'(5')-carboxyfluorescein, 4'(5')-chlorofluorescein, 4'(5')-methylfluorescein, 4'(5')-sulfofluorescein, 4'(5')-aminorhodol, 4'(5')-carboxyrhodol, 4'(5')-chlororhodol, 4'(5')-methylrhodol, 4'(5')-sulforhodol; 4'(5')-aminorhodamine 110, 4'(5')-carboxyrhodamine 110, 4'(5')-chlororhodamine 110, 4'(5')-methylrhodamine 110, 4'(5')-sulforhodamine 110 and 4'(5')thiorhodamine 110. "4'(5')" means that at the 4 or 5' position the hydrogen atom on the carbon atom is substituted with a specific organic group or groups as previously listed. A 7-Amino, or sulfonated coumarin derivative may likewise be employed.

Alternatively, the analytes and substrates that may be used in accordance with the principles of the present invention may possess a chemiluminescent moiety. Suitable chemiluminescent moieties include acridinium esters, ruthenium complexes, metal complexes (e.g., U.S. Pat. Nos. 6,281,021, 5,238,108 and 5,310,687), oxalate ester-peroxide combination, etc.)

Alternatively, the analytes and substrates that may be used in accordance with the principles of the present invention may possess a colorimetric moiety. Suitable colorimetric moieties include thiopeptolides, anthroquinone dyes, 2 methoxy 4 (2 nitrovinyl) phenyl β-2 acetamido 2 deoxy β D glucopyranoside; ammonium 5 [4 (2 acetamido 2 deoxy β D glucopyranosyloxy) 3 methoxy phenylmethylene] 2 thioxothiazolin 4 one 3 ethanoate hydrate; 4{2 [4 (β D glucosyl pyranosyloxy) 3 methoxy phenyl]vinyl} 1 methylquinolinium iodide, 2 methoxy 4 (2 nitrovinyl) phenyl β D galactopyranoside, 2 {2 [4 (β D galactopyranosyloxy)3 methoxyphenyl]vinyl} 1 methyl quinolinium iodide, 2 {2 [4 (β D galactopyranosyloxy)3 methoxyphenyl]vinyl} 3 methyl benzothiazolium iodide, 2 {2 [4 (β D glucopyranosyloxy) 3 methoxyphenyl]vinyl} 1 methyl quinolinium iodide, 2 {2 [4 (β D glucopyranosyloxy) 3 methoxyphenyl] vinyl} 1 propyl quinolinium iodide, 2 {2 [4 (β D glucopyranosyloxy) 3 methoxyphenyl]vinyl} 3 methyl benzothiazolium iodide, ammonium 5 [4 β D glucopyranosyloxy) 3 methoxy phenylmethylene] 2 thioxothiazolin 4 one 3 ethanoate hydrate, 2 methoxy 4 (2 nitrovinyl) phenyl acetate, 2 methoxy 4 (2 nitrovinyl) phenyl propionate, 5 [4 propanoyloxy) 3,5 dimethoxy phenylmethylene] 2 thioxothiazolin 4 one 3 ethanoate, 5 [4 butanoyloxy) 3,5 dimethoxy phenylmethylene] 2 thioxothiazolin 4 one 3 ethanoate, 5 [4 decanoyloxy) 3,5 dimethoxy phenylmethylene] 2 thioxothiazolin 4 one 3 ethanoate, 5 [4 dodecanoyloxy) 3,5 dimethoxy phenylmethylene] 2 thioxothiazolin 4 one 3 ethanoate, 5 [4 tetradecanoyloxy) 3,5 dimethoxy phenylmethylene] 2 thioxothiazolin 4 one 3 ethanoate, Pyridinium 4 {2 [4 (phosphoroyloxy) 3,5 dimethoxyphenyl]vinyl} 1 propyl quinolinium iodide, Pyridinium 5 (4 phosphoryloxy 3,5 dimethoxy phenylmethylene) 3 methyl 2 thioxothiazolin 4 one, etc.

Alternatively, the analytes and substrates that may be used in accordance with the principles of the present invention may comprise detectable ions (including H ion) or other analytes.

The uptake-enhancing agents of the present invention are employed in concentrations sufficient to improve or facilitate the conducting of the analysis. The preferred concentrations of glycerol for the purposes of the present invention range from about 5% to about 60% (v/v), more preferably from about 20% to about 50% (v/v), still more preferably from about 25% to about 40% (v/v), still more preferably from about 30% and about 35% (v/v), and most preferably about 30% (v/v). It is preferable to add the glycerol to the assay with minimal mixing. Such concentrations provide improved signal to noise ratios, and permit the assay to be conducted using lower concentrations or amounts of assay substrates, thereby reducing assay cost.

The preferred concentrations of DMSO for the purposes of the present invention range from about 5% to about 60% (v/v), more preferably from about 20% to about 60% (v/v), still more preferably from about 30% to about 50% (v/v), still more preferably from about 35% to about 55% (v/v), and most preferably about 40% (v/v). It is likewise preferable to add the DMSO to the assay with minimal mixing. As discussed below, the concentration of DMSO employed is substantially greater than that of DMSO solubilizing agent.

The preferred concentrations of trehalose for the purposes of the present invention range from about 0.5 M to about 1.5 M, and more preferably from about 1.0 M to about 1.5 M.

The preferred concentrations of glutamate (provided, for example as potassium glutamate) for the purposes of the present invention range from about 0.25 M to about 2.0 M, more preferably from about 1.0 M to about 2.0 M, still more preferably from about 1.1 M to about 1.75 M, still most preferably about 1.3 M.

The preferred concentrations of betaine for the purposes of the present invention range from about 0.3 M or greater, more preferably about 1.5 M or greater, more preferably about 1.8 M or greater, still more preferably about 2.0 M or greater. Betaine concentrations of about 1.8 M to about 2.2 M are particularly preferred.

The preferred concentrations of ethylene glycol for the purposes of the present invention range from about 2 M to about 7 M.

The preferred concentrations of threitol for the purposes of the present invention range from about 1 M to about 5 M or more, and more preferably from about 0.25 M to about 2.5 M or more. Threitol concentrations of less than 5 M are particularly preferred.

The preferred concentrations of ribose for the purposes of the present invention range from about 0.4 M to about 4 M, and more preferably about 2 M to about 3 M.

The preferred concentrations of trimethylamine N-oxide for the purposes of the present invention range from about 0.4 M to about 4 M or more, and more preferably from about 2 M to about 4 M or more. Trimethylamine N-oxide concentrations of about 2 M to less than 7 M are particularly preferred.

In one embodiment of the invention, the improved methods and reagents of the present invention facilitate the detection of enzymatically functional proteases rather than the mere physical presence of protein (as is detected in antibody ELISA formats, etc.), and can provide a distinct measure of cellular activities.

The compositions and methods of the present invention may be used in any of a wide variety of assay formats, and are amenable to automated, or high throughput processing (using, for example a Biomek® work station (Beckman Coulter)). The assay may be used to provide an indication of the presence of a disease, of the progress of a disease, the efficacy of a drug, or of cell differentiation. As discussed below, the compositions and methods of the present invention have particular utility for improving the cell-based assays described by Lucas et al. (U.S. Pat. No. 5,698,411) and Landrum et al. (U.S. Pat. No. 5,976,822).

In accordance with the principles of the present invention, cells (especially metabolically active cells) are contacted with an assay reagent that contains a preselected substrate or analyte for a preselected enzyme and an effective concentration of an uptake-enhancing agent. The presence of the uptake-enhancing agent permits the assay to more efficiently assay or detect preselected substrate or analyte that has been acted upon by the preselected enzyme.

The improved assay methods of the present invention can be conducted as a homogeneous assay not requiring generation of cell extracts, centrifugation or washing steps. It is compatible with standard cell culture growth media and gives results in as little as 15 minutes with as few as $1.5 \times 10^3$ cells. It is particularly compatible with assays involving flowcytometry. One aspect of the present invention relates to the extension of prior assay methods to permit the assaying of cells in single vessels, arrays of vessels (particularly "microtiter plates," such as a conventional 96-well microtiter plate, etc.), or arrays of cells on surfaces. Thus, a single assay may be run and the difference between the beginning state and the end state of a substrate, such as the cleavage of a single substrate by a target enzyme to yield free peptide and fluorescent indicator dye, can be determined. Alternatively, a series of assays can be conducted each with a pattern matrix of several substrates reacted with an abnormal cell versus the same matrix reacted with a normal cell.

In one embodiment, only a single enzyme is assayed at a time. Alternatively, multiple enzymes (e.g., 2 or more, and more preferably 5 or more enzymes) may be assayed either simultaneously or sequentially. In this regard, the methods and reagents of the present invention are particularly suitable for use in applications in which multiple enzymes are simultaneously assayed. In one embodiment, such multiplexing is accomplished through the use of substrates whose detection are discrete (for example an assay involving a fluorescent substrate and a second assay involving a chemiluminescent substrate). Alternatively, substrates may be employed whose detection involves different wavelengths of fluorescent, WV, visible light, etc. Such detection can be accomplished using multiple detectors, multipass filters, gratings, or spectrally distinct fluors (see, e.g., U.S. Pat. No. 5,759,781), etc. In one embodiment, the individual enzymes being assayed will be separately assayed (e.g., caspases 1, 3, 6, 8, and 9), so that determinations of the individual activities will be provided. Alternatively, a sum of all such enzymes being assayed will be detected (e.g., the sum of caspases 1, 3, 6, 8, and 9), and provided as a composite sum of such activity.

II. Use of Cellprobe Reagents that Contain a Blocking Group to Improve Cell-Based Assays In a second another embodiment of the invention, the use of cellprobe reagents that contain a blocking group (for example, an N-benzyloxycarbonyl blocking group (a "Cbz" group)) has been found to enhanced assay sensitivity when used in concert with the above-described uptake-enhancing agents.

In general such cellprobe reagents contain an "indicator group" and one, two, three, four or even more "leaving groups." The "indicator group" of the compound is a chemical moiety selected for its ability to have a first state when joined to the leaving group, and a second state when the leaving group is cleaved from the indicator group by the enzyme. The indicator group is preferably excitable (caused to fluoresce) at a wavelength about the visible range, for example, at wavelength between about 450 to 500 nanometers (nm). The indicator group will usually emit in the range of about 480 to 620 nm, preferably 500 to 600 nm and more preferably 500 to 550 nm. Auto-fluorescence of the cell is most prevalent below about 500 nm. The indicator group is preferably derived from fluorescent, colorimetric, bioluminescent or chemiluminescent compounds. The indicator group is preferably quenched when joined to the leaving group. The term quenched means that the indicator group has substantially less fluorescence or chemiluminescence when joined to the leaving group compared to its fluorescence or chemiluminescence after the leaving group has been cleaved. For example, the enzyme glutamyltranspeptidase reacts with gammaglutamyl amino acid peptide giving gamma glutamic acid; trypsin cleaves the peptide at the arginine residue; aminopeptidase-M hydrolyzes the peptide at the aliphatic amino acid residue; and chymotrypsin cleaves the peptide at the phenylalanine residue. Suitable fluorogenic indicator compounds include xanthine compounds. Preferably, the indicator compounds are rhodamine 110; rhodol; fluorescein; and coumarin, and their derivatives. While, for convenience, the invention is described below with respect to fluorescent leaving groups, it will be appreciated that the leaving groups may alternatively be enzymatic, colorimetric, bioluminescent, chemiluminescent, paramagnetic, luminescent, radioactive, etc.

Each "leaving group" of the compound is a chemical moiety selected so that it will be cleaved by the enzyme to be analyzed. For such embodiment, compounds having a molecular weight of less than about 5,000 are preferred. The leaving group is selected according to the enzyme that is to be assayed. The leaving group will preferably have utility for assaying any of a variety of cellular enzymes, including proteases, caspases, glycosidases, glucosidases, carbohydrases, phosphodiesterases, phosphatases, sulfatases, thioesterases, pyrophosphatases, lipases, esterases, nucleotidases and nucleosidases, as listed above.

The leaving group is preferably selected from amino acids, peptides, saccharides, sulfates, phosphates, esters, phosphate esters, nucleotides, polynucleotides, nucleic acids, pyrimidines, purines, nucleosides, lipids and mixtures thereof. For example, a peptide and a lipid leaving group can be separately attached to a single assay compound such as rhodamine 110. Other leaving groups suitable for the enzyme to be assayed can be determined empirically or obtained from the literature. See, for example, Mentlein, R. et al., H. R., "Influence of Pregnancy on Dipeptidyl Peptidase IV Activity (CD26 Leukocyte Differentiation Antigen) of Circulating Lymphocytes", *Eur. J. Clin. Chem. Clin. Biochem.*, 29, 477–480 (1991); Schon, E. et al., *Eur. J. Immunol.*, 17, 1821–1826 (1987); Ferrer-Lopez, P. et al., "Heparin Inhibits Neutrophil-Induced Platelet Activation Via Cathepsin", *J. Lab Clin. Med.* 119(3), 231–239 (1992); and Royer, G. et al., "Immobilized Derivatives of Leucine Aminopeptidase and Aminopeptidase M.", *J. Biol. Chem.* 248(5), 1807–1812 (1973). These references are hereby incorporated by reference in their entirety.

Examples of such regents include (Cbz-Phe-Arg-NH)$_2$-rhodamine and (Cbz-Pro-Arg-NH)$_2$-rhodamine, which have particularly use in assays for human plasmin and human thrombin, respectively (Leytus, S. P. et al., "New class of sensitive and selective fluorogenic substrates for serine proteases," Biochem. J. 215:253–260 (1983)).

Derivatives of the tetrapeptides ala-ala-pro-leu and ala-ala-pro-val (Beckman Coulter) are preferred assay compounds for assaying the activity of the closely related enzymes leukocyte elastase and pancreatic elastase (leukocyte elastase is also known as neutrophil elastase, EC 3.4.21.37; pancreatic elastase is also known as EC 3.4.21.36) (Stein, R. L. et al. 1987, "Catalysis by human leukocyte elastase: Mechanistic insights into specificity requirements," Biochem. 26:1301–1305; Stein, R. L. et al. 1987, "Catalysis by human leukocyte elastase: Proton inventory as a mechanistic probe," Biochem. 26:1305–1314). Elastases are defined by their ability to cleave elastin, the matrix protein that gives tissues the property of elasticity. Human leukocyte elastase is a serine protease that is a major component of neutrophil granules and is essential for defense against infection by invading microorganisms (Bode, W. et al. 1989, "Human leukocyte and porcine pancreatic elastase: X-ray crystal structures, mechanism, substrate specificity and mechanism-based inhibitors," Biochem. 28:1951–1963)

Aspartic acid-Rho110 (Beckman Coulter) is a preferred assay compound for assaying the activity of the Ca-dependent enzyme aminopeptidase A (aspartate aminopeptidase, angiotensinase A, EC 3.4.11.7). Aminopeptidase A is found in both soluble and membrane-bound forms. Aminopeptidase A is known to cleave the N-terminal aspartic acid amino acid of angiotensin I or II (Jackson, E. K. et al., 1995, "Renin and Angiotensin" in Goodman and Gilman's The Pharmacological Basis of Therapeutics, Ninth Edition McGraw-Hill, NY). Aminopeptidase A is also identical to BP-1/6C3 (Wu, Q. et al., 1991. "Aminopeptidase A activity of the murine B-lymphocyte differentiation antigen BP-1/6C3," Proc. Natl. Acad. Sci, USA. 88: 676–680), a molecule found on early lineage B cells but not on mature lymphocytes. BP-1/6C3 may have a role in the ability to support long-term growth of B cells (Whitlock, C. A., et al., 1987. "Bone marrow stromal cell lines with lymphopoietic activity express high levels of a pre-B neoplasia-associated molecule," Cell 48: 1009–1021.

The conversion of non-fluorescent dichlorofluorescein diacetate (DCFH-DA) (Beckman Coulter) to the highly fluorescent compound 2',7'-dichlorofluorescein (DCF) is a preferred assay compound for monitoring the oxidative burst in polymorphonuclear leukocytes and for determining the presence of peroxides formed through such oxidative bursts (Bass, D. A. et al. "Flow cytometric studies of oxidative product formation by neutrophils: a graded response to membrane stimulation." J. Immunol. 130: 1910–1917). The enzymes responsible for the oxidative burst are rapidly activated in stimulated neutrophils (Weiss, S. J. 1989, "Tissue destruction by neutrophils," N. Eng. J. Med. 320: 365–376). DCFH,PMA Oxidative Burst contains the compound phorbol myristate acetate (PMA), an analogue of the cellular signaling molecule diacylglycerol (DAG) (Alberts, B. et al., Molecular Biology of the Cell, 2nd Edition. Garland Publishing, Inc. New York, pg 704). Therefore, the presence of PMA stimulates processes mediated by DAG, including the oxidative burst. Additionally, resting cells do not have free peroxides and the production of peroxides is rapidly activated by many cell stimuli including the presence of the bacteria or other foreign organisms (Weiss. S. J. 1989, "Tissue destruction by neutrophils," N. Eng. J. Med. 320: 365–376). The production of peroxides due to the oxidative burst can by artificially stimulated by the addition of the compound phorbol myristate acetate (PMA) to the neutrophils (CellProbe substrate DCFH,PMA Oxidative Burst). DCFH Peroxides can be used to investigate the effect of other compounds on the oxidative burst including the chemotactic peptide f-met-leu-phe and the yeast product zymosan.

Fluorescein diacetate (FDA) (Beckman Coulter) is a preferred assay compound for assaying the activity of many different non-specific esterases in human tissues (Coates, P. M. et al., 1975, "A preliminary genetic interpretation of the esterase isozymes of human tissues," Ann. Hum. Genet. Lond. 39: 1–20). Acetate esterase activity measured with -Napthyl acetate has been used together with other esterase activities to identify leukocyte cell types and is generally high in normal monocytes and megakaryocytes and in blast cells of acute myelomonocytic leukemia, acute monocytic leukemia and acute erythroleukemia. Nelson, D. A. et al., 1990, "Leukocyte esterases in Hematology," 4th Edition, Williams, Beutler, Erslev and Lichtman, Eds. McGraw-Hill.

Fluorescein di-galactopyranoside (Beckman Coulter) is a preferred assay compound for assaying the activity of the galactosidase enzymes (β-galactosidase is also known as lactase, β-D-galactoside galactohydrolase, EC 3.2.1.23; α-galactosidase is also known as melibiase, α-D-galactoside galactohydrolase, EC 3.2.1.22) (Jongkind, J. F. et al., 1986, "Detection of acid-b-galactosidase activity in viable human fibroblasts by flow cytometry," Cytometry 7:463–466). Galactosidase enzymes are lysosomal enzymes that cleave terminal sugar residues from several physiological substrates, including glycoproteins. Gal galactosidase contains forms of the substrate that are hydrolyzed by both b-galactosidase and a-galactosidase. Impaired galactosidase activity leads to accumulation of partially digested glycoproteins in the lysosomes (Cotran, R. S. et al., 1994, Robbins Pathologic Basis of Disease, 5th Edition. W.B. Saunders Co. pages 138–140). The lysosomes become enlarged, and disrupt normal cell function. The impaired galactosidase activity may be due to mutations in the galactosidase genes or in the processing and transport mechanisms of galactosidase to the lysosomes.

Glycine-phenylalanine-glycine-alanine-Rho110 (Beckman Coulter) is a preferred assay compound for assaying the activity of the collagenase group of proteolytic enzymes in a screen of several tetrapeptide derivatives. Collagenases are enzymes that digest the collagens: macromolecules that form highly organized structures in connective tissue and extracellular matrix. Collagenases and other members of the matrix metalloproteinase family contribute to physiological processes such as postpartum involution of the uterus, wound healing, joint destruction in arthritis, tumor invasion and periodontitis. The collagenases are Zn+2 dependent metallo-enzymes that are synthesized in a pro-enzyme inactive form (Woessner, J F Jr. 1991. Matrix metalloproteinases and their inhibitors in connective tissue remodeling. FASEB J. 5: 2145–21541). The production of HOCl during the neutrophil oxidative burst has been postulated as one mechanism for collagenase activation in vivo.

The assay compound, fluorescein di-glucuronide (Beckman Coulter) is hydrolyzed by the lysosomal enzyme b-glucuronidase (β-glucuronidase is also known as β-D-glucuroniside glucuronosohydrolase, EC 3.2.1.31). A derivative of β-glucuronide has been used to measure degranulation in polymorphonuclear lymphocytes (PMNs) in a test of the ability of different non-steroidal anti-inflammatory drugs (NSAIDS) to inhibit PMN functions (Kankaanranta, H. et al., 1994, "Effects of non-steroidal anti-inflammatory drugs on polymorphonuclear leukocyte functions in vitro: focus on fenamates," Naunyn-Schmiedeberg's Arch Pharmacol. 350: 685–691). Peripheral blood T-lymphocytes display higher β-glucuronidase activity that peripheral blood B-lymphocytes (Crockard, A. et al., 1982, "Cytochemistry of acid hydrolases in chronic B- and T-cell leukemias," Am. J. Clin. Pathol. 78:437–444). Fluorescein di-glucuronide is a negatively charged compound. To help other derivatives of sugars pass through cell membranes in assays of β-glucosidase, a lysomotropic detergent (N-dodecylimidazole) was used (Kohen, E. et al., 1993, "An in situ study of beta-glucosidase activity in normal and gaucher fibroblasts with fluorogenic probes," Cell Biochem. and Function. 11:167–177).

Glycine-proline-Rho110 (Beckman Coulter) is a preferred assay compound for assaying the activity of the serine protease dipeptidyl peptidase IV (DPP IV; Xaa-Pro-dipeptidyl-aminopeptidase, Gly-pro naphthylamidase, EC 3.4.14.5). The membrane bound form of DPP IV is also known as the T-cell activation cell surface marker CD26 (Fleischer, B., 1994, "CD26: a surface protease involved in T-cell activation," Immunol. Today. 15: 180–184). The proteolytic activity of DPP IV may play an essential role in the signaling function of CD26 (Hegen, M. et al., 1993, "Enzymatic activity of CD26 (dipeptidylpeptidase IV) is not required for its signalling function in T cells," Immunobiology. 189: 483–493; Tanaka, T. et al., 1993, "The costimulatory activity of the CD26 antigen requires dipeptidyl peptidase IV enzymatic activity," Proc. Natl. Acad. Sci. USA. 90: 4586–4590). DPP IV cleaves the N-terminal dipeptide from oligopeptides with sequences analogous to the N-terminal sequence of signaling molecules IL-1b, IL-2 and TNF-b, but does not have activity against intact recombinant molecules (Hoffmann, T. et al. 1993, "Dipeptidyl peptidase IV (CD 26) and aminopeptidase N (CD 13) catalyzed hydrolysis of cytokines and peptides with N-terminal cytokine sequences," FEBS Letters. 336: 61–64). Studies of dipeptidyl peptidase IV activity with GP DPP IV suggest that DPP IV is upregulated in mature thymocytes and among thymocytes which are undergoing programmed cell death (apoptosis) (Ruiz, P. et al., 1996, "Cytofluorographic evidence thatthymocyte dipeptidyl peptidase IV (CD26) activity is altered with stage of ontogeny and apoptotic status," Cytometry. 23: 322–329).

Glycine-proline-leucine-glycine-proline-Rho110 (Beckman Coulter) is a preferred assay compound for assaying the activity of the collagenase group of proteolytic enzymes. Collagenases are Zn+2 dependent metallo-enzymes that are synthesized in a pro-enzyme inactive form 1. (Collagenases digest the collagens: macromolecules that form highly organized structures in connective tissue and extracellular matrix. Collagenases and other members of the matrix metalloproteinase family contribute to physiological processes such as postpartum involution of the uterus, wound healing, joint destruction in arthritis, tumor invasion and periodontitis (Woessner, J. F. Jr., 1991, "Matrix metalloproteinases and their inhibitors in connective tissue remodeling," FASEB J. 5: 2145–2154). In a detailed study of the mechanism of hydrolysis of fluorescent derivatives of GPLGP, Kojima et al. found that a collagenase-like peptidase cleaved the substrate at the peptide bond between leu and gly (Kojima, K. et al., 1979, "A new and highly sensitive fluorescence assay for collagenase-like peptidase activity," Anal. Biochem. 100: 43–50).

Lys-Rho 110 (Beckman Coulter) is a preferred assay compound for assaying the activity of aminopeptidase B (EC 3.4.11.6). The aminopeptidases are a group of enzymes which hydrolyze peptide bonds near the N-terminus of polypeptides (International Union of Biochemistry and Molecular Biology. Enzyme Nomenclature. 1992. Academic Press, San Diego). Aminopeptidase B has been purified from the cytosolic fraction of human liver and skeletal muscle and shown to act on synthetic lysyl- or arginyl-substrates. Aminopeptidase B is activated by Cl-1 or Br-1 ions and inhibited by chelating agents and bestatin (Sanderink, G. J. et al., 1988, "Human Aminopeptidases: A Review of the Literature. J. Clin. Chem. Clin. Biochem. 26: 795–807).

Fluorescein di-phosphate (Beckman Coulter) is a preferred assay compound for assaying the activity of the enzyme acid phosphatase (Acid phosphatase is also known as EC 3.1.3.2) (Rotman, B. et al., 1963, "Fluorogenic substrates for b-D-galactosidases and phosphatases derived from fluorescein (3,6-dihydroxyfluoran) and its monomethyl ether,". Proc. Nat. Acad. Sci. USA 50:1–6). Assays of acid phosphatase activity have been used together with assays of esterase activity to identify many different cell types. Monocytes, neutrophils and T-lymphocytes have relatively high acid phosphatase activity while B-lymphocytes have relatively low acid phosphatase activity. (Crockard, A. et al., 1982, "Cytochemistry of acid hydrolases in chronic B- and T-cell leukemias," Am. J. Clin. Pathol. 78:437–444; Li, C. Y. et al., 1970, "Acid phosphatase isoenzyme in human leukocytes in normal and pathologic conditions," J. Histochem. Cytochem. 18:473–481). In addition, blast cells of acute promyelocytic leukemia and acute myelomonocytic leukemia have been shown to have relatively high acid phosphatase activity (Nelson, D. A. et al. 1990, "Leukocyte esterases in Hematology Fourth Edition," Williams W J, Beutler E, Erslev A J and Lichtman M A eds. McGraw Hill, New York.

Arginine-Rho 110 (Beckman Coulter) is a preferred assay compound for assaying the activity of aminopeptidase B (arginyl aminopeptidase, EC 3.4.11.6). The aminopeptidases are a group of enzymes which hydrolyze peptide bonds near the N-terminus of polypeptides (International Union of Biochemistry and Molecular Biology. Enzyme Nomenclature. 1992. Academic Press, San Diego). Aminopeptidase B has been purified from the cytosolic fraction of human liver and skeletal muscle and shown to act on synthetic lysyl- or arginyl-substrates. Aminopeptidase B is activated by Cl-1 or Br-1 ions and inhibited by chelating agents and bestatin (Sanderink, G. J. et al., 1988, "Human Aminopeptidases: A Review of the Literature," J. Clin. Chem. Clin. Biochem. 26: 795–807.

Arg-Gly-Glu-Ser-Rho110 (Beckman Coulter) is a preferred assay compound for assaying the activity of the closely related enzymes leukocyte elastase and pancreatic elastase (leukocyte elastase: neutrophil elastase, EC 3.4.21.37 pancreatic elastase: EC 3.4.21.36). Leukocyte elastase is a serine protease that is a major component of neutrophil granules and is essential for phagocytosis and defense against infection by invading microorganisms (Bode, W. et al., 1989, "Human leukocyte and porcine pancreatic elastase: X-ray crystal structures, mechanism, substrate specificity and mechanism-based inhibitors," Biochem. 28: 1951–1963). The tetrapeptide RGES is part of the sequence of fibronectin (Gartner, T. K. et al., 1985, "The tetrapeptide analogue of the alpha chain and decapeptide analogue of the gamma chain of fibrinogen bind to different sites on the platelet fibrinogen receptor," Blood. 66 Suppl 1: 305a), which is cleaved by human leukocyte elastase (McDonald, J. A. et al., 1980, "Degradation of fibronectin by human leukocyte elastase," J. Biol. Chem. 255: 8848–8858).

The assay compound, threonine-proline-Rho 110 (Beckman Coulter) was identified as a substrate for cathepsin C (dipeptidyl-peptidase I, EC 3.4.14.1) and cathepsin G (EC 3.4.21.19) by a screen of many different dipeptide derivatives. Cathepsin C (DPPI) is a lysosomal cysteine peptidase that is found in relative abundance in cytotoxic cells (Thiele, D. L. et al., 1990, "Mechanism of L-leucyl-L-leucine methyl ester-mediated killing of cytotoxic lymphocytes: Dependence on a lysosomal thiol protease, dipeptidyl peptidase I, that is enriched in these cells," Proc. Natl. Acad. Sci. USA. 87: 83–87). Cathepsin G is a serine endopeptidase that is a major component of the azurophil granules of polymorphonuclear leukocytes. Cathepsin G activity is high in promonocytic cells, but reduced in mature monocytes (Hohn, P. A. et al., 1989, "Genomic organization and chromosomal localization of the human cathepsin G gene," J. Biol. Chem. 264: 13412–13419.

Other suitable leaving groups are described in Table 1 of U.S. Pat. No. 5,698,411 (Lucas, et al.) and Landrum et al. (U.S. Pat. No. 5,976,822), and include: (Acetyl-α-D-glucopyranosyl) Rho 110; (Adenine)$_2$ Rho 110; (Adenosine Monophosphate)$_2$ Rho 110; (Adenosine) Rho 110; (B-D-Galactopyranoside)$_2$ Rho 110; (B-D-glucuronide)$_2$ Rho 110; (Butyrl-Thiocholine)$_2$; (Cytosine)$_2$ Rho 110; (Guanine)$_2$ Rho 110; (H Gly)$_2$ Rho 110; (H Gly-Arg)$_2$ Rho 110; (H Gly-Gly-Arg)$_2$ Rho 110; (H Gly-Leu)$_2$ Rho 110; (H Gly-Phe-Gly-Ala)$_2$ Rho 110; (H Gly-Pro-Leu-Gly-Pro)$_2$ Rho 110; (H-Gly)$_2$-4'chloro-Rho 110; (H-Gly)$_2$ Rho 110; (H-Gly-Ala-Ala-Ala)$_2$ Rho 110; (H-Gly-Arg)$_2$ Rho 110; (H-Gly-Gly-Arg)$_2$ Rho 110; (H-Gly-Pro)$_2$ Rho 110; (H-Gly-Pro-Leu-Gly-Pro) Rho 110; (Hippuryl-His-Leu)$_2$ Rho 110; (H-L Ala-Ala-Ala-Ala)$_2$ Rho 110; (H-L Ala-Pro)$_2$ Rho 110; (H-L Leu-Leu-Arg)$_2$ Rho 110; (H-L Lys-Ala)$_2$ Rho 110; (H-L Lys-Ala)$_2$ Rho 110.Sulfo.4TFA; (H-L Lys-Ala-Lys-Ala)$_2$ Rho 110; (H-L Pro-Arg)$_2$ Rho 110; (H-L-Ala)$_2$-4'chloro-Rho 110; (H-L-Ala)$_2$-Rho 110; (H-L-Ala-Ala)$_2$ Rho 110; (H-L-Ala-Ala-Ala)$_2$ Rho 110; (H-L-Ala-Ala-Pro-Ala)$_2$ Rho 110; (H-L-Ala-Ala-Tyr)$_2$ Rho 110; (H-L-Ala-Arg-Arg)$_2$ Rho 110; (H-L-Ala-Gly)$_2$ Rho 110; (H-L-Ala-Phe-Lys)$_2$ Rho 110; (H-L-Ala-Pro)$_2$-Rho 110; (H-L-Ala-Pro-Ala)$_2$ Rho 110; (H-L-Arg)$_2$ Rho 110; (H-L-Arg-Arg)$_2$ Rho 110; (H-L-Arg-Gly-Glu-Ser)$_2$ Rho 110; (H-L-Asp)$_2$-Rho 110; (H-L-Cys)$_2$-Rho 110; (H-L-Gln-Ser)$_2$ Rho 110; (H-L-Glu)$_2$-Rho 110; (H-L-Glu-Cys-Gly)$_2$ Rho 110; (H-L-Glu-Gly-Arg)$_2$ Rho 110; (H-L-Glu-Gly-Phe)$_2$ Rho 110; (H-L-Glu-Lys-Lys)$_2$ Rho 110; (H-L-Gly-Arg)$_2$-Rho 110; (H-L-Leu)$_2$-4'chloro-Rho 110; (H-L-Leu)$_2$ Rho 110; (H-L-Leu-Gly)$_2$ Rho 110; (H-L-Leu-Gly-Leu-Gly)$_2$ Rho 110; (H-L-Leu-Leu-Arg)$_2$ Rho 110; (H-L-Lys)$_2$ Rho 110; (H-L-Lys)$_2$-Rho 110; (H-L-Lys-Ala)$_2$-Rho 110; (H-L-Lys-Ala)$_2$ Rho 110-Sulfo; (H-L-Lys-Ala-Arg-Val)$_2$ Rho 110; (H-L-Lys-Ala-Arg-Val-Phe)$_2$ Rho 110; (H-L-Lys-Ala-Lys-Ala)$_2$-Rho 110.6TFA; (H-L-Lys-Pro)$_2$ Rho 110; (H-L-Lys-Pro)$_2$-Rho 110; (H-L-Met)$_2$ Rho 110; (H-L-Phe-Arg)$_2$ Rho 110; (H-L-Pro)$_2$ Rho 110; (H-L-Pro)$_2$-Rho 110; (H-L-Pro-Arg)$_2$ Rho 110; (H-L-Pro-Phe-Arg)$_2$ Rho 110; (H-L-Ser)$_2$ Rho 110; (H-L-Serine Phosphate)$_2$ Rho 110; (H-L-Threonine Phosphate)$_2$ Rho 110; (H-L-Thr-Pro)$_2$ Rho 110; (H-L-thyroxine)$_2$ Rho 110; (H-L-Tyrosine Phosphate)$_2$ Rho 110; (H-L-Val-Leu-Lys)$_2$ Rho 110; (H-L-Val-Lys-Val-Lys)$_2$ Rho 110; (H-L-Val-Pro-Arg)$_2$ Rho 110; (H-L-Val-Ser)$_2$ Rho 110; (H-Pro-Arg)$_2$-Rho 110; (N-Acetyl MET)$_2$ Rho 110; (N-Acetyl-L-Ala)$_2$ FL; (Phosphatidyl-choline)$_2$ Rho 110; (Saturated Hydrocarbon)$_2$ Rho 110; (Thymidine)$_2$ Rho 110; (Triacetin)$_2$ Rho 110; (Unsaturated Hydrocarton)$_2$ Rho 110; (Z-Ala-Ala)$_2$ Rho 110; (Z-Ala-Gly)$_2$ Rho 110; (Z-Thr-Pro)$_2$ Rho 110; (γ-Glu)$_2$ Rho 110; FL(Acetyl-Choline)$_2$; FL(butyrate)$_2$; FL(chloroacetate)$_2$; FL(chlorobutyrate)$_2$; FL(choline)$_2$; FL(heptanoate)$_2$; FL(hexanoate)$_2$; FL(palmitate)$_2$; FL(phosphate)$_2$; FL(propionate)$_2$; FL(valerate)$_2$; Fluorescein (acetate)$_2$; H-L-Leu Rhodol; H-L-Leu Rhodol; Rho 110 (phosphate)$_2$; Rho 110 (Phosphatidyl-choline)$_2$; Rho 110 (Phosphatidylinositol)$_2$; and Rho 110(AMP)$_2$.

When the leaving group of the assay compound is a salt complex, it will significantly improve the transmission of the assay compound into the cell (Lucas, et al. (U.S. Pat. No. 5,698,411) and Landrum et al. (U.S. Pat. No. 5,976,822)). The selection of an appropriate salt complex requires a consideration of the compatibility with the cell, solubility in the aqueous media, and cleavage by the enzyme. Care is required in the selection of the peptide salt since isoenzymes have been found to be specific in their recognition of particular salts.

Leaving groups for saccharidases are preferably prepared by the synthesis of monosaccharides, oligosaccharides or polysaccharides comprising between one and about ten sugar residues of the D-configuration. Examples of useful sugars are monosaccharides-pentoses; ribose; deoxyribose; hexose: glucose, dextrose, galactose; oligosaccharides-sucrose, lactose, maltose and polysaccharides like glycogen and starch. The sugar can be an alpha or beta configuration containing from 3 to 7 and preferably 5 to 6 carbon atoms. Analogs of these sugars can also be suitable for the invention. Preferably, the D-configuration of the monosaccharide or disaccharide is utilized. The monosaccharide or disaccharide can be natural or synthetic in origin.

Leaving groups for nucleases, nucleotidases, and nucleosidases are preferably prepared by the synthesis of nucleic acids, purines, pyrimidines, pentose sugars (i.e., ribose and deoxyribose) and phosphate ester. Examples are adenine, guanine, cytosine, uracil and thymine. Leaving groups for restriction enzymes would include polynucleotides. The nucleic acids contain a purine or pyrimidine attached to a pentose sugar at the 1-carbon to N-9 purine or N-1 pyrimidine. A phosphate ester is attached to the pentose sugar at the 5' position. Analogs of these building blocks can also be used.

Leaving groups for lipases are preferably prepared by the synthesis of simple lipids, compound lipids or derived lipids. Simple lipids can be esters of fatty acids, triglycerides, cholesterol esters and vitamin A and D esters. Compound lipids can be phospholipids, glycolipids (cerebrosides), sulfolipids, lipoproteins and lipopolysaccharides. Derived lipids can be saturated and unsaturated fatty acids and mono or diglycerides. Analogs of these lipids can also be used. Examples of lipids are: triglycerides—triolein, fatty acids—linoleic, linolenic and arachidonic; sterols—testosterone, progesterone, cholesterol; phospholipids—phosphatidic acid, lecithin, cephalin (phosphatidyl ethanolamine) sphingomyleins; glycolipids—cerebosides, gangliosides.

Leaving groups for esterases are preferably prepared by the synthesis of carboxylic acids comprising between 2 and 30 carbon atoms. The carboxylic acids can be saturated or unsaturated. The carboxylic acid preferably contains 2 to 24 carbons and more preferably 4 to 24 carbon atoms. Analogs of theses carboxylic acids can also be used. The carboxylic acids can be natural or synthetic in origin. Examples are butyric, caproic, palmitic, stearic, oleic, linoleic and linolenic.

Leaving groups for phosphatases are preferably prepared by the synthesis of phosphates, phosphatidic acids, phospholipids and phosphoproteins. Analogs of these compounds can also be used. Examples are ATP, ADP, AMP and cyclic AMP (c-AMP).

Leaving groups for peptidases are preferably prepared by the synthesis of peptides comprising between one and about ten amino acid residues of the L-configuration. Typically, it has been found that the synthesis of peptides having more than about six amino acids produces a low yield. However, where the yield is acceptable, peptides of greater length can be employed. The amino acids preferably contain 2–10 and preferably 2–8 carbon atoms. Analogs of these amino acids can also be suitable for the invention. If the amino acids are chiral compounds, then they can be present in the D- or L-form or also as a racemate. Preferably, the L-configuration of the amino acid is utilized. The amino acids of the oligopeptide can be natural and/or of synthetic origin. Amino acids of natural origin, such as occur in proteins and peptide antibiotics, are preferred. Synthetic amino acids can also be used, such as pipecolic acid, cyclohexylalanine, phenylglycine, .alpha.-aminocyclohexylcarboxylic acid, hexahydrotyrosine, norleucine, or ethionine.

Suitable methods for synthesizing, purifying, and preparing such compounds for use in cell-based assays are described in Lucas, et al. (U.S. Pat. No. 5,698,411) and Landrum et al. (U.S. Pat. No. 5,976,822), herein incorporated by reference.

II. Improvement to the Assays of Lucas et al. (U.S. Pat. No. 5,698,411) and Landrum et al. (U.S. Pat. No. 5,976,822)

As stated above, the present invention provides a way to improve assays such as those described by Lucas et al. (U.S. Pat. No. 5,698,411) and Landrum et al. (U.S. Pat. No. 5,976,822), herein incorporated by reference, in which enzyme activity is determined using a substrate "Assay Reagent" (especially a CellProbe™ reagent (Beckman-Coulter, Inc.)) that is internalized into a metabolically active cell and generates a detectable fluorescent response when acted upon by the enzyme.

The inclusion of uptake-enhancing agents in such Assay Reagent has been found to result in increased detection sensitivity, and to allow kinetic as well as end-point assay determinations of proteases such as activated Caspases. The concentration of such agents in such Assay Reagent is selected so as to be sufficient to induce or promote the uptake of compounds into the cell. Suitable methods of isolating and preparing such cells are provided by Lucas et al. (U.S. Pat. No. 5,698,411) and Landrum et al. (U.S. Pat. No. 5,976,822), herein incorporated by reference. Due to the sensitivity of the assay of the present invention, 5,000 or even fewer cells can be employed, although larger numbers of cells can be employed if desired.

The preferred assay compounds for the purposes of the invention comprise CellProbe Reagents™ of Beckman Coulter, Inc., which are constructed with two, three, four or more leaving groups, each of which is a substrate for the target enzyme. The bonds between the leaving groups and indicator group are cleaved one at a time, resulting in the formation of first a monoconjugated indicator group molecule, then a free dye. Alanine-Rho 110 (Beckman Coulter) is a preferred assay compound for assaying aminopeptidase M (alanine aminopeptidase, aminopeptidase N, EC 3.4.11.2) activity. The aminopeptidases are a group of enzymes which hydrolyze peptide bonds near the N-terminus of polypeptides. The cell surface marker CD13 is aminopeptidase M (Look, A. T. et al. 1989, "Human myeloid plasma membrane glycoprotein CD13 (gp150) is identical to aminopeptidase N," J Clin Invest 83: 1299–1307). Aminopeptidase M may have a role in myeloid cell regulation as a negative regulator through inactivation of bioactive peptides (Ashmun R A and Look A T. 1990, "Metalloprotease Activity of CD13/Aminopeptidase N on the Surface of Human Myeloid Cells," Blood 75: 462–469). This was illustrated in an experiment where a specific inhibitor of aminopeptidase M increased such processes as phagocytosis and immune responses to antigen and tumor cell stimuli.

The Assay Reagent is preferably designed to have an osmolality, ionic strength and pH that is compatible with metabolically active cells. The preferred pH for assay compounds for particular enzymes is included in Table 1 of Lucas, et al. (U.S. Pat. No. 5,698,411) and Landrum et al. (U.S. Pat. No. 5,976,822), herein incorporated by reference.

The chemical nature of the buffer is important to the reactivity of the assay compound with the cellular enzymes. For example, Hanks solution is reported to be a better cellular buffer than cacodylic acid at 0.1 M concentration for amino peptidase (see, Lucas, et al. (U.S. Pat. No. 5,698,411) and Landrum et al. (U.S. Pat. No. 5,976,822)). More specifically, by utilizing Hanks solution, at pH 7.5, it has been further found that the assay compound has a higher sensitivity for the targeted enzyme. In addition, the assay compound hydrolysis by the enzyme occurs at an increased rate of reaction. Although Hanks solution contains calcium chloride at a concentration of 1.26 mM, calcium chloride has been found in the case of aminopeptidase to be inhibitory to the enzyme reaction with the assay compound, $(H-L-Asp)_2$ rhodamine 110, at concentrations of approximately 10 mM. Buffer components that show no inhibitory effect to the cells can be used. Suitable buffer components are N-tris(hydroxymethyl)methyl-2-aminoethanesulfonic acid (TES), Hanks balanced salt and 2-N-morpholinoethanesulfonic acid (MES), tris-glycine, HEPES, glycine sodium hydroxide, and cacodylate. The preferred buffer components are MES for acidic solutions, Hanks for neutral solutions, and glycine sodium hydroxide for basic solutions. A metabolic energy source such as a sugar (glucose) can be added if desired. Preferred buffers, co-factors, modulators and inhibitors for particular enzymes are described in Lucas, et al. U.S. Pat. No. 5,698,411) and Landrum et al. (U.S. Pat. No. 5,976, 822).

In addition to the above-described Assay Compounds, and uptake-enhancing agent(s), such Assay Reagent will preferably comprise one or more additional components such as a buffer, cofactor, modulator, inhibitor, or an activator for increasing the activity of the target enzymes over non-targeted enzymes.

The Assay Compound will preferably be soluble in the Assay Reagent. Solubility is measured by light scatter using the percent transmittance of light (or absorbance) through the mixture of the media and assay compound. As measured on a spectrophotometer, the Assay Compound should have a background color at a concentration to be used in an assay of less than 1000, preferably less than 800, and most preferably less than 500 milliabsorbance units at 340 nanometers (25.degree. C.) blanked against distilled or deionized water. The Assay Compound will usually be used at a concentration of 0.5 to 10 mM. A useful concentration for determining solubility is 5 mM.

A large excess quantity of the Assay Compound with respect to enzyme is preferred. If an insufficient amount of the Assay Compound is provided, the enzyme reaction will completely hydrolyze the Assay Compound and the dynamic range of the assay will be limited. The resulting indicator compound will have a limited fluorescence duration. However, when an excess of the Assay Compound is employed, the enzyme reaction will continuously hydrolyze the assay compound and the fluorescence duration will continue during the enzyme reaction. This provides the advantage of having a longer time period in which to sense for one or more reaction states of the assay compound.

The Assay Reagent may additionally comprise solubilizing components and retention components to improve the enzyme assay results. A solubilizing agent is included in order to facilitate the transfer of the Assay Compound into the metabolically active cells. The solubilizing component is present in an amount effective to enable the assay compound to pass through the cell lipid bilayer without detrimentally affecting the cell. The solubilizing agent should be carefully chosen so as not to cause cell lysis or cell death. When the assay compound has a background color (at the concentration to be used in an assay) greater than 1,000, greater than 800 or greater than 500 milliabsorbance units, a solubilizing component may be used to lower the background color to less than 1,000, less than 800 or less than 500 milliabsorbance units. However, the concentration of the solubilizing component is limited. If a high concentration of the solubilizing component is used, metabolically active cells will be lysed. If a low concentration of the solubilizing component is used, sufficient solubility of the assay compound will not be attained. The effective amount of solubilizing component may be empirically determined, but is typically less than 10.0% by weight of the assay compound.

Suitable solubilizing components include 0.1% BRIJ 35® (ICI Americas, Inc.) (Polyoxyethylene lauryl ether); 0.2% PLURONIC 25 R8® (BASF Wyandotte) (Ethylene oxide with hydrophobic base from propylene oxide and propylene glycol); 0.1% TRITON X100® (Rohm and Haas Company) (Octylphenoxy polyethoxyethanol); 0.1% TWEEN 20 (ICI Americas, Inc.) (Polyoxyethylene sorbitan monolaurate (polysorbate 20); 0.1% Polyethylene Glycol, 5% Dimethyl Sulfoxide, 4.5% Mannitol.

When using a solubilizing component, certain difficulties have been encountered. While the solubilizing component facilitates the transmission of the assay compound into the metabolically active cell, the solubilizing component will also facilitate the expulsion of the fluorescent indicator group compound from the metabolically active cell. The expulsion of the indicator group will have the negative effect of permitting non-enzyme containing cells to absorb free dye. When this occurs, the accuracy of an enzyme assay is compromised. In addition, the electronic configuration and polar nature of the liberated indicator dye influences its ability to be retained within the cell. Retention of the dye is important for proper detection.

As described by Lucas et al. (U.S. Pat. No. 5,698,411) and Landrum et al. (U.S. Pat. No. 5,976,822), this problem can be averted through the additional inclusion of a retention component in the Assay Reagent. The retention component will comprise at least one agent that will inhibit a cell pump mechanism for expressing extracellular material. Such cell pumps include the multiple drug response pump, calcium channel pump, sodium pump, potassium pump and ATPase pump. Suitable retention components include trifluoperazine.HCl, prochlorperazine.maleate, and chlorpromazine.HCl to inhibit the multiple drug response pump; verapar-nil.hydrochloride to inhibit the calcium channel pump; and digoxin ($C_{41}H_{64}O_{14}$), digoxin derivatives, such as ouabain ($C_{29}H_{44}O_{12}$), and strophatidin ($C_{23}H_{32}O_6$) to inhibit the sodium, potassium and ATPase pump.

An acceptable improved Assay Reagent for use in accordance with the assays described by Lucas et al. (U.S. Pat. No. 5,698,411) and Landrum et al. (U.S. Pat. No. 5,976, 822), will therefore preferably comprise the following characteristics:

(1) its Assay Compound will exhibit a low level of native free fluorescence that is absorbed by the cells, non-specifically. Thus, there should be a low level of fluorescent impurities such as free indicator compounds. The acceptable and preferred levels of these impurities have already been described;

(2) its Assay Compound will be stable over time so that it does not need to be used shortly after it is prepared. Certain impurities and certain reagent additives can increase the rate of autohydrolysis which increases the fluorescence of the reagent;

(3) its Assay Compound will support a sufficiently high rate of reaction with the enzyme being measured so that fluorescence generated as a result of reaction between the enzyme and the reagent can be easily measured. In one aspect, the reaction rate should be sufficiently high that fluorescence generated as a result of cleavage of the leaving group inside the cell is at least 2 times, preferably at least 10 times, more preferably at least 50 times and most preferably at least 100 times greater than other non-specific fluorescence generated in the assay. In another aspect, the reagent should contain an assay compound which is blocked by, for example, a Cbz group; and (4) an uptake-enhancing agent, present at a concentration sufficient to cause such uptake.

IV. Uses of the Invention

As will be appreciated from the preceding description, the present invention has potential use in the following clinical applications: diagnosis of cervical cancer, diagnosis of viral replication in HIV patients, diagnosis of HIV infected blood in blood supply, diagnosis of TB infected HIV patients, improved blood differential, differential diagnosis of viral from bacterial infections, differential diagnosis of Lupus from rheumatoid arthritis, differential diagnosis between rheumatoid arthritis from osteoarthritis, diagnosis of vasculitis, diagnosis of cardiovascular disease, monitoring of chemotherapeutic efficacy, diagnosis of Hodgkins Disease, confirmation of gene implantation and diagnosis of transplant rejection. For example, to contribute to the diagnosis of cervical cancer, the activity of enzymes related to the presence of cervical cancer can be assayed. To contribute to the diagnosis of viral replication in patients, HIV or Hepatitis replication in blood cells can be monitored. A sensitive measure of HIV or Hepatitis replication can be important as a predictor of rapid movement into the AIDS state from the HIV infected stage of the disease. Since the virus replicates in the lymphocytes and monocytes, monitoring specific enzyme levels can make the monitoring both inexpensive and reproducible. A low cost screening methodology can be devised whereby blood can be subjected to HIV or Hepatitis antibody testing and testing by the method of this invention.

This invention also has utility for the differential diagnosis of viral from bacterial (e.g., *M. tuberculosi*) infections. Many patients have an elevated temperature and it is not known whether the temperature is from a viral or bacterial origin. The differential diagnosis between viral and bacterial infections assists the clinician in the management of these patients by allowing the physician to apply the proper therapy on an as needed basis.

This invention has further utility for differential diagnosis of Lupus from rheumatoid arthritis/drug monitoring in rheumatoid arthritis and Lupus patients. In the early course of disease, the symptoms for Lupus Erythematosis and rheumatoid arthritis are sufficiently similar that differential diagnosis of the disease is difficult, especially when a Lupus patient has early arthritic involvement. This has clinical consequences since it delays the administration of the correct therapy. Lupus can be a clinically aggressive disease and it is beneficial to the patient to have the correct diagnosis at an early date. These patients have different enzymes in activated states meaning that this methodology is the modality to use for a differential diagnosis. Additionally, monitoring the therapeutic application of steroid drugs can be of benefit to the patient.

This invention has still further utility for differential diagnosis between rheumatoid arthritis from osteoarthritis. Rheumatoid arthritis is an aggressive autoimmune disease which results in destruction of the panus of the joint. Osteoarthritis is a degenerative disease of the aging joint which is not immune mediated. Since immune cells migrate throughout the body, this methodology provides an early differential diagnosis between these two diseases. This is important since the correct therapy for each disease is different.

Moreover, this invention has utility for diagnosis of vasculitis. Vasculitis is an autoimmune disease of blood vessels generally in the extremities. Patients with this disease typically have nondescript complaints of pain which do not permit diagnosis until considerable damage has been completed on the vascular system by the immune cells. Since it is an autoimmune disease caused by circulating immune cells, the disclosed methodology can provide the needed information to make an early diagnosis.

Furthermore, this invention has utility for monitoring of cardiovascular disease. Atherosclerosis results in the deposition of platelets and other cellular components into the walls of coronary vessels. This process results in the loss of elasticity of the vessels and eventually in death. It has been shown that in these patients, as many as 20% of the platelets are in the activated state. Evaluation of platelets can permit the identification of patients with active atherosclerotic processes ongoing and permit administration of disease altering drugs.

Moreover, this invention has utility for monitoring of chemotherapeutic efficacy. Patients undergoing chemotherapeutic therapy have altered enzyme patterns which indicates that this change in enzyme levels can be used to monitor the effectiveness of chemotherapy.

In addition, this invention has utility for diagnosis of Hodgkins disease. The practice of this invention can be useful to monitor the stages of Hodgkins disease.

Furthermore, this invention has utility for diagnosis of transplant rejection. The practice of this invention can be useful to monitor the acceptance of an organ transplant. All patients are given immunosuppressants to prevent organ rejection and therefore it is difficult to distinguish infection from rejection.

Moreover, this invention has utility for monitoring for metastatic invasion. It has been found that tumor cells have different patterns of enzymes from normal cells in the same tissue. Identification of the types of enzymes is useful and important for predicting metastatic potential and invasion. Tumor cells in circulating blood can be useful to predict the progression of the disease.

The media into which the assay Reagent is introduced must be compatible with the cell so that the cell can remain metabolically active in the media for at least the duration of the assay, and will preferably be sterile and free of endotoxin and chemicals that adversely affect the physiology of the cell. The Assay Compound is preferably completely soluble in the media at the concentration at which it is used. The Assay Compound is preferably used in concentrations up to the saturation or the suspension level or before turbidity occurs. The media may be physiological saline or a buffered solution (phosphate buffered saline) in which the assay compound and other additives are dissolved. The media should preferably include a buffer agent so that the pH of the Assay Reagent is maintained at a point that is appropriate for the enzyme assay.

The concentration of the cells in the media should be high enough to provide a reading of the desired number of cells within the desired time period, taking into consideration the speed of the instrument that is being used. For current flow cytometry techniques, a concentration of about three million cells per milliliter is appropriate to yield a measurement of about 10,000–15,000 cells in about 1–2 minutes.

The Assay Compound is generally employed in concentrations in excess of the amount which can be completely hydrolyzed by the quantity of enzyme within the time of the assay. An Assay Compound concentration that is too high may have a negative effect on enzyme activity, since the leaving group can be a negative feedback inhibitor to enzyme activity.

The Assay Compound leaving group concentration in a cellular optimization is determined using Km (a known rate constant) and $V_{MAX}$ (maximum velocity) calculations. The leaving group is preferably present in an amount from about 2 to about $100 \times V_{MAX}$ and most preferably from about 2 to about 10 times the amount which can be completely hydrolyzed by the enzyme within the duration of the assay period.

The assay may be conducted either as a rate determination or as an end point determination. Rate determinations are preferred, because they are generally less affected by auto-fluorescence. Consequently, a rate determination assay is more sensitive and precise. In a rate determination, the fluorescence of the Assay Compound-cell analyte mixture may be determined promptly after the cell analyte is contacted with the Assay Compound. The ability to see a signal and distinguish it from background noise determines the initial starting point of data collection and the final data point is preferably determined at the point where the slope of the reaction rate changes, typically more than 2%.

Most cellular reactions do not strictly obey zero-order kinetics. Most cellular enzymes show a delay between the time of exposure of the cells to the Assay Compound, and the ability to detect a signal that is greater than the background noise. Cellular enzymatic reactions that do not obey zero order kinetics are still useful measurements as first order, pseudo first order, or initial rate measurements. Multiple enzymes in a reaction (mixed reactions) are displayed by slope changes during the time course being monitored.

In an endpoint determination, the enzyme hydrolysis reaction is allowed to proceed for a predetermined length of time, usually at $V_{MAX}$. The reaction time can be calculated based on whether the reaction is zero order or first order kinetics using Michaelis—Menton methodology. Alternatively, the reaction time can also be adjusted by a different elapsed time for pseudo-first order reactions.

A number of factors may decrease the reliability of the assay, and yield false positive, or erroneous indications of enzymatic activity. These include (i) extended reaction between the cell analyte and the Assay Compound; (ii) another, non-targeted enzyme that is cleaving the leaving group; (iii) auto-hydrolysis of the Assay Compound; (iv) inhibitors or stimulators that are present and undetected; (v) cells that are no longer metabolically active, or dead; (vi) mixed populations of cells; (vii) a transfusion of the patient before sampling; (viii) non-specific dye uptake by negative cells; and (ix) background fluorescence. The creation of false negatives, or false indications of a lack of enzymatic activity, can be caused by (i) insufficient reaction between the cell analyte and the Assay Compound, (ii) a hypo-osmotic media leading to a decrease in cell activity; (iii) a cell that is no longer metabolically active; (iv) burst cells; and (v) the presence of inhibitors to the target enzyme.

The efficiency or reliability of the assays can be significantly improved if reaction conditions are adjusted to maximize the activity of the assayed enzyme relative to other non-assayed enzymes which might otherwise compete for the leaving group. More specifically, the targeted enzyme can be involved in a chain cascade reaction of enzymes sequentially coupled to other enzymes, as in a multi-enzyme reaction cascade.

The reaction conditions can be adjusted to maximize the efficiency of the pathway, or to decrease the efficiency of competing pathways. Such conditions preferably include at least one of pH, choice of form of Assay Compound, temperature, osmotic pressure, ionic strength, and reaction time. The pH at which an enzyme is most efficient can be determined from the literature, or determined empirically. The form of Assay Compound can be important since some enzymes require non-derivatized, natural structures for recognition of binding and reaction, whereas other enzymes are less selective. More specifically, derivatization and salt formation of the Assay Compound are important properties for solubilization, enzyme recognition and protection from auto-hydrolysis.

A reaction run using the same data collection window without the enzyme source will determine auto-hydrolysis of the substrate and therefore the potential for negative cells to absorb the dye non-specifically resulting in false positive.

The time of the assay is typically less than 30 minutes, preferably less than 20 minutes, usually between 5 seconds and 20 minutes, and most preferably between about 10 seconds and about 5 minutes. Some enzyme systems, such as esterase and phosphatase, can react with the Assay Compound in shorter periods of time due to concentrations of enzymes found in the cell. The reaction time should be limited so that the effects of cellular expulsion of the indicator compound will be avoided.

The temperature at which the assay is performed must be high enough to retain viability and to ensure enzyme activity, but not so high as to cause degradation or other deleterious reactions involving the leaving group, the enzyme, or other components of the mixture. Particular enzymes, or enzymes in particular pathways, are more reactive at particular temperatures. The temperature is preferably maintained between about 30° C. to about 40° C., more preferably between about 35° C. and about 38° C., and most preferably between about 36° C. to about 38° C.

The ionic strength of the assay mixture should be selected so as to avoid shriveling, crenating or bursting (stromatolysing) of the cells, and also to maximize the activity of the assayed enzyme relative to other, non-assayed enzymes. An ionic strength that is too low could deplete metals such as $Ca^{+2}$, $Mg^{+2}$, and $Zn^{+2}$, or cause insufficient amounts of anions such as $Cl^{-1}$, $NO_3^{-1}$, $SO_4^{-2}$ and $PO_4^{-3}$ which are the cofactors that can be used to improve enzymatic activity. The ionic strength of the Assay Reagent is preferably between about 0.1 to 0.3 µM.

The fluorescence reading is made after the reaction has occurred or after a specific period of time. Typically, the reaction is stopped by immersing the reaction container in ice and water which cools the cells to about 0° C. Sensing for one or more reaction states by fluorescence determinations confirms cleavage of the indicator group by the enzyme. Fluorescence can be detected using a fluorometer, fluorescent microscope, or by other means. For example, the fluorescence determinations may be performed on a Image Analysis System (IAS). The IAS is a microscope based system that measures fluorescence known to those skilled in the art. A representative example of an IAS is the Metamorph™ by Universal Imaging Corporation, West Chester, Pa.

Flow cytometers may also be used. The structure and operation of flow cytometers is also well documented in the literature. Alternatives to traditional FC include slit-scan FC and stopped-flow FC. The flow cytometer can perform additional measurements in addition to a single wavelength fluorescence measurement. The flow cytometers can be equipped to measure fluorescence at two or more separate wavelengths. Such readings are useful to perform assays according to the invention when using more than one Assay Compound, or for using cell surface markers, such as monoclonal antibodies, to determine cell morphology. Additional wavelengths are useful to measure the activity of another enzyme, which can be a peptidase or a different enzyme such as a phosphatase, saccharidase, nucleotidase, esterase, or lipidase. Such additional tests are useful for simultaneously characterizing disease states, and for determining cell morphology and cell types.

In the experiments described in the examples below, a fluorometer (FLUOstar Galaxy (BMG Laboratories, Inc., Durham, N.C.)) was used to measure the very low fluorescence levels that are generated by the assay. The fluorometer is tuned to the excitation and emission wavelengths of the particular indicator being used. Preferred compounds such as rhodamine 110 and fluorescein have excitation and emission wavelengths of about 495 to 498 nm (excitation) and 520 to 525 nm, respectively.

Many suitable methods may be used to prepare samples for assays in accordance with the methods of the present invention (see, for example, Lucas et al. (U.S. Pat. No. 5,698,411) and Landrum et al. (U.S. Pat. No. 5,976,822)). Where a flow cytometer is employed, the cells can be separated by size or granularity. The activity of the target enzyme is then assayed using the Assay Reagent. Two samples are allowed to proceed at different times and the reaction is stopped. The difference in fluorescence permits the calculation of a rate. Alternatively, the flow cytometer can be used to separate the cells by size and granularity. Cell morphology is determined by a fluorescence assay with a monoclonal antibody marker. The rate of the hydrolysis of the Assay Compound is then determined. In a third alternative method, the cells can be analyzed by size, granularity, two colors and backgate fluorescence (see, Duque, R. E., "Flow Cytometric Analysis of Lymphomas and Acute Leukemias", Annals of the New York Academy of Sciences, Clinical Flow Cytometry, 677, pp. 309–325 (Mar. 20, 1993). The size and granularity of the cell are separated by a flow cytometer using light scatter and/or with surface markers, such as monoclonal antibodies. A series of cell populations are determined, with rearrangement of the histogram to identify the disease and normal cells. The activity of the enzyme is then assayed. In a fourth alternative, the activity of the target enzyme in a population of cells over time is assayed. The results of the assay are compared to reference values that are characteristic of the range of enzyme activity established in normal males and females to permit a determination of whether the activity of the target enzyme is within normal ranges, or is characteristic of a particular morphology or disease state. Artificial intelligence or Non-Negative Least Squares (NNLS) programs and analysis of variance (ANOVA) programs, etc. may be used to facilitate such determinations. Such determinations may be used to establish the presence or absence of a single enzyme, or may be used to assess the presence of a combination of enzymes as a complex interplay of metabolic systems All publications and patents mentioned in this specification are herein incorporated by reference to the same extent as if each individual publication or patent application was specifically and individually indicated to be incorporated by reference. Having now generally described the invention, the same will be more readily understood through reference to the following examples, which are provided by way of illustration, and are not intended to be limiting of the present invention, unless specified.

Having now generally described the invention, the same will be more readily understood through reference to the following examples, which are provided by way of illustration, and are not intended to be limiting of the present invention, unless specified.

EXAMPLE 1

Improved Assay using Glycerol or 67 DMSO

The improved detection of the assays of the present invention resulting from the use of glycerol at concentrations greater than 5% was demonstrated by conducting assays for apoptosis. To initiate such assays, 25 µl of Caspase CellProbe Reagent™ (Beckman Coulter) was added to a suspension of $1 \times 10^5$ U-937 cells in 110 µl of culture medium in a 96-well microtiter plate. Cells were incubated for one hour, and had been either uninduced or induced by prior incubation in the presence of 2.5 µM Camptothecin. The final concentration of the Caspase CellProbe Reagent™ was 30 µM.

Figure 2:
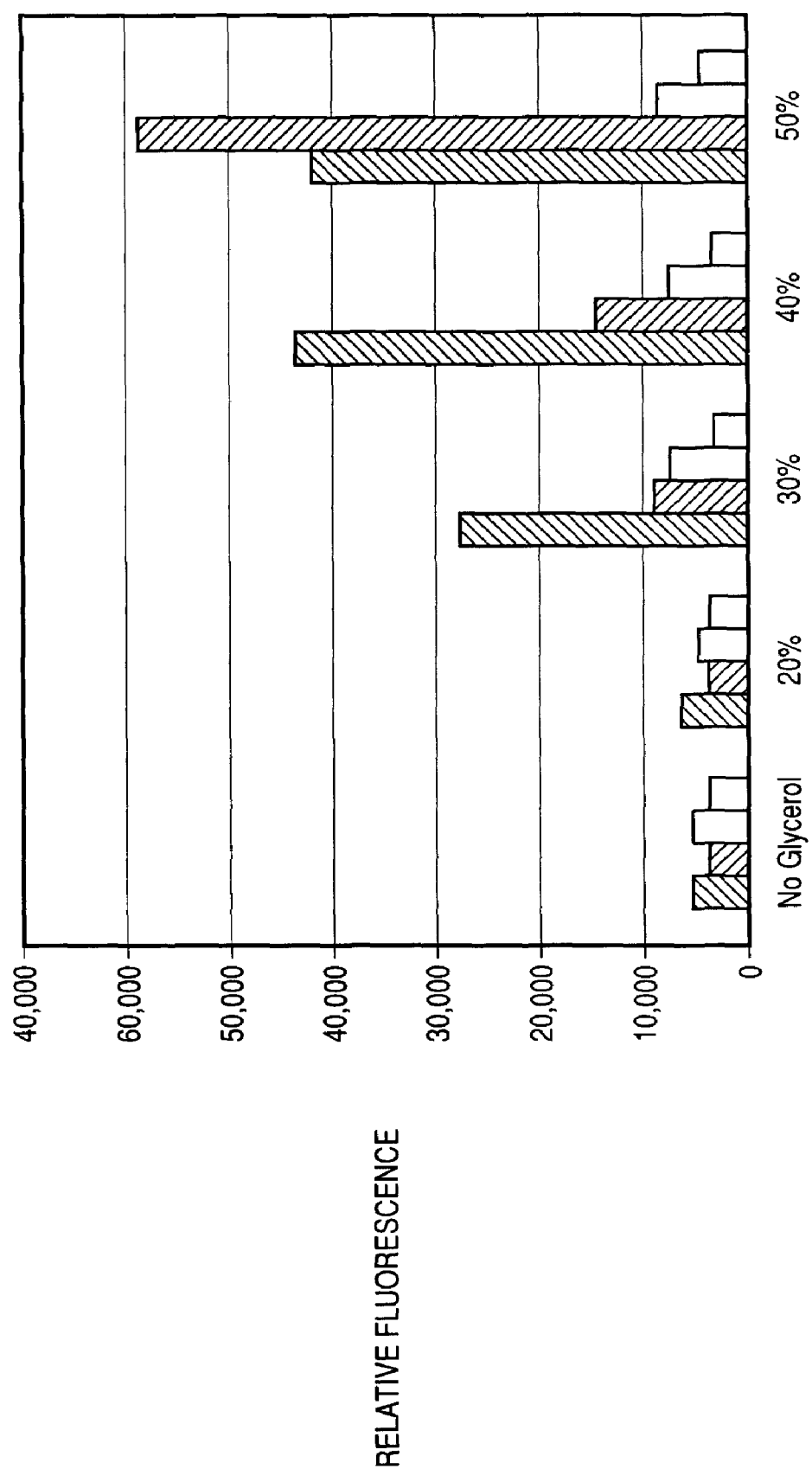
FIG. 2 shows the effect of glycerol on a Caspase 6 CellProbe™ assay with U-937 suspension cells.
Figure 3:
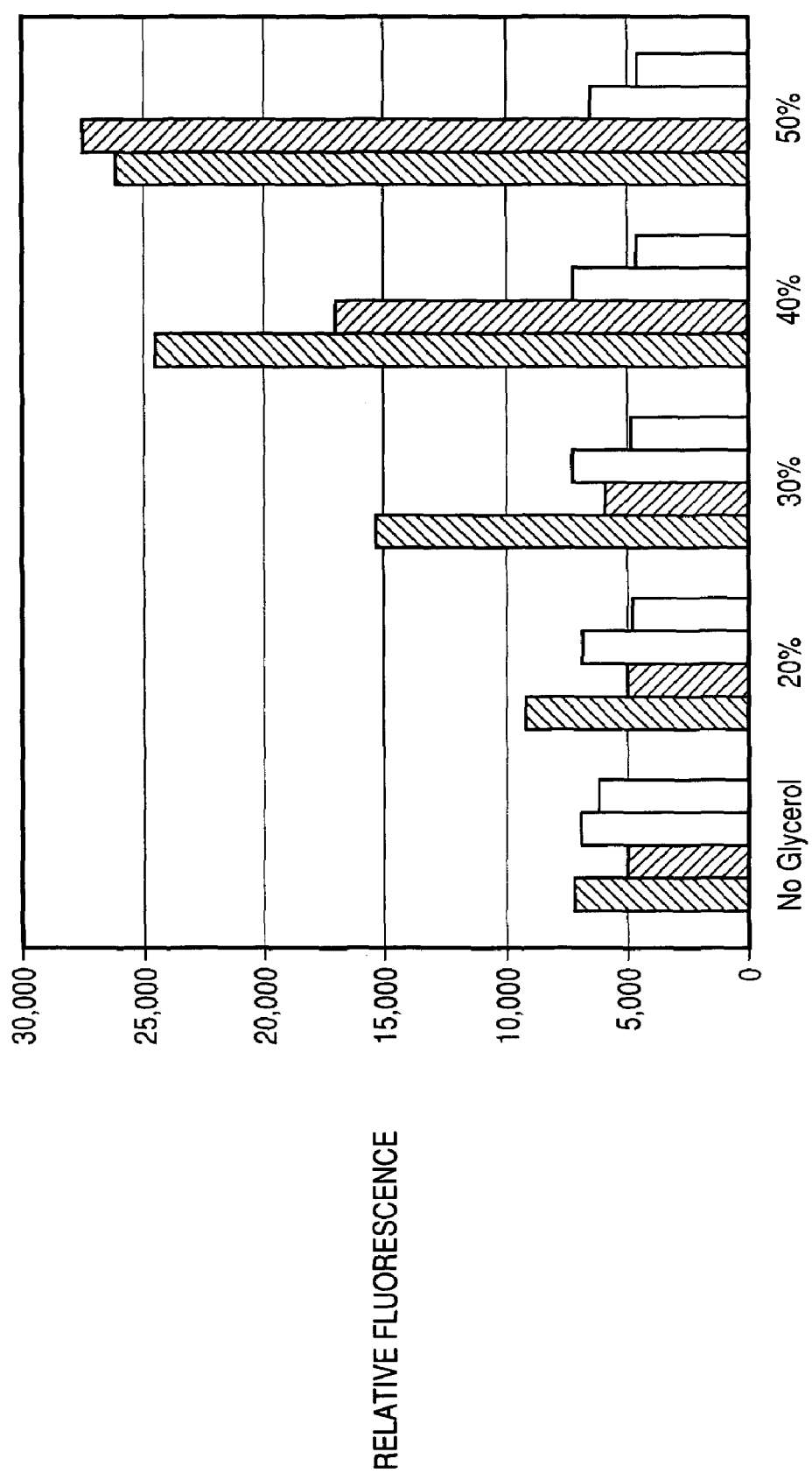
FIG. 3 shows the effect of glycerol on a Caspase 1 CellProbe™ assay with U-937 suspension cells.

As can be seen in FIGS. 1–3, a dramatic improvement in detection of Caspase 1, 3 and 6 activity is realized at various optimal glycerol concentrations. In the Figures, the 5 series of columns reflect results obtained with no glycerol, 20% glycerol, 30% glycerol, 40% glycerol and 50% glycerol. The individual columns (left to right) within each data series reflect results for: unmixed sample—induced; unmixed sample—uninduced; mixed sample—induced; and mixed sample—uninduced.

For Caspase 3 (FIG. 1), a significant relative signal increase is noticed by raising the glycerol concentration from 0 to 50%, and it is of greater magnitude when the sample is unmixed. In the case of Caspase 6 (FIG. 2) and Caspase 1 (FIG. 3) however, added unmixed glycerol concentrations of ~50% and ~40% respectively appear to have a deleterious effect.

Figure 4:
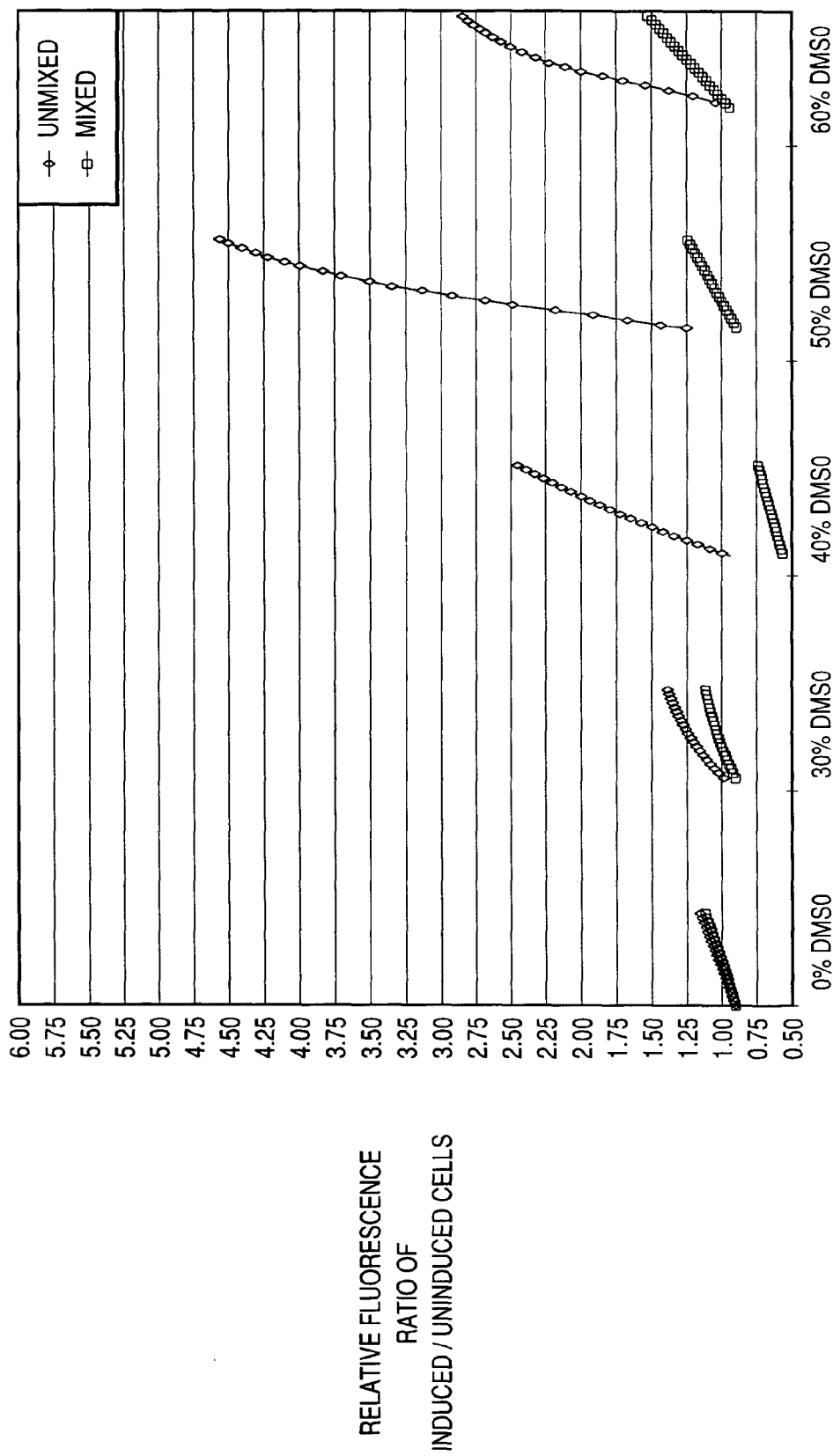
FIG. 4 shows the DMSO concentration effect as added with 30 μm final cell probe in a one hour kinetic assay detection of Caspase using U-937 cells.

Assays for apoptosis were similarly performed in order to demonstrate the improved detection of the assays of the present invention resulting from the use of DMSO at concentrations greater than 5% were demonstrated by conducting assays for apoptosis. The results shown in FIG. 4 is of kinetic signal from twenty fluorescence readings of the one hour assay. In FIG. 4, lines containing a diamond (♦) denote unmixed samples; lines containing boxes (■) and appearing as thick lines denote mixed samples. The signal ratio decrease observed above the 50% DMSO concentration is due to an increase in non-specific signal from the uninduced cell controls.

In sum, inclusion of DMSO or glycerol in the Assay Reagent at concentrations greater than 5% increases the density of the added solution. After the addition of these denser solutions to the cell culture media in the assay, they subside or layer over adherent or settled suspension cells to be used. If careful addition of the solution occurs with minimal mixing, maximal signal enhancing effect is observed. Any immediate mixing of added reagent solution resulting in a homogeneous concentration dramatically reduces the effectiveness of the method (see FIGS. 1–5 and 7).

EXAMPLE 2

Improved Assay Using Glutamate

The improved detection of the assays of the present invention resulting from the use of glutamate at concentrations ranging from 1.5 M to 2.0 M is demonstrated by conducting assays for apoptosis using HeLa cells. To initiate 110 such assays, Caspase CellProbe Reagent™ (Beckman Coulter) is added to a suspension of $1.5 \times 10^4$ HeLa cells/well in a 96-well microtiter plate. The final concentration of the Caspase CellProbe Reagent™ was 30 µM. Reaction is for 1 hour.

Figure 5:
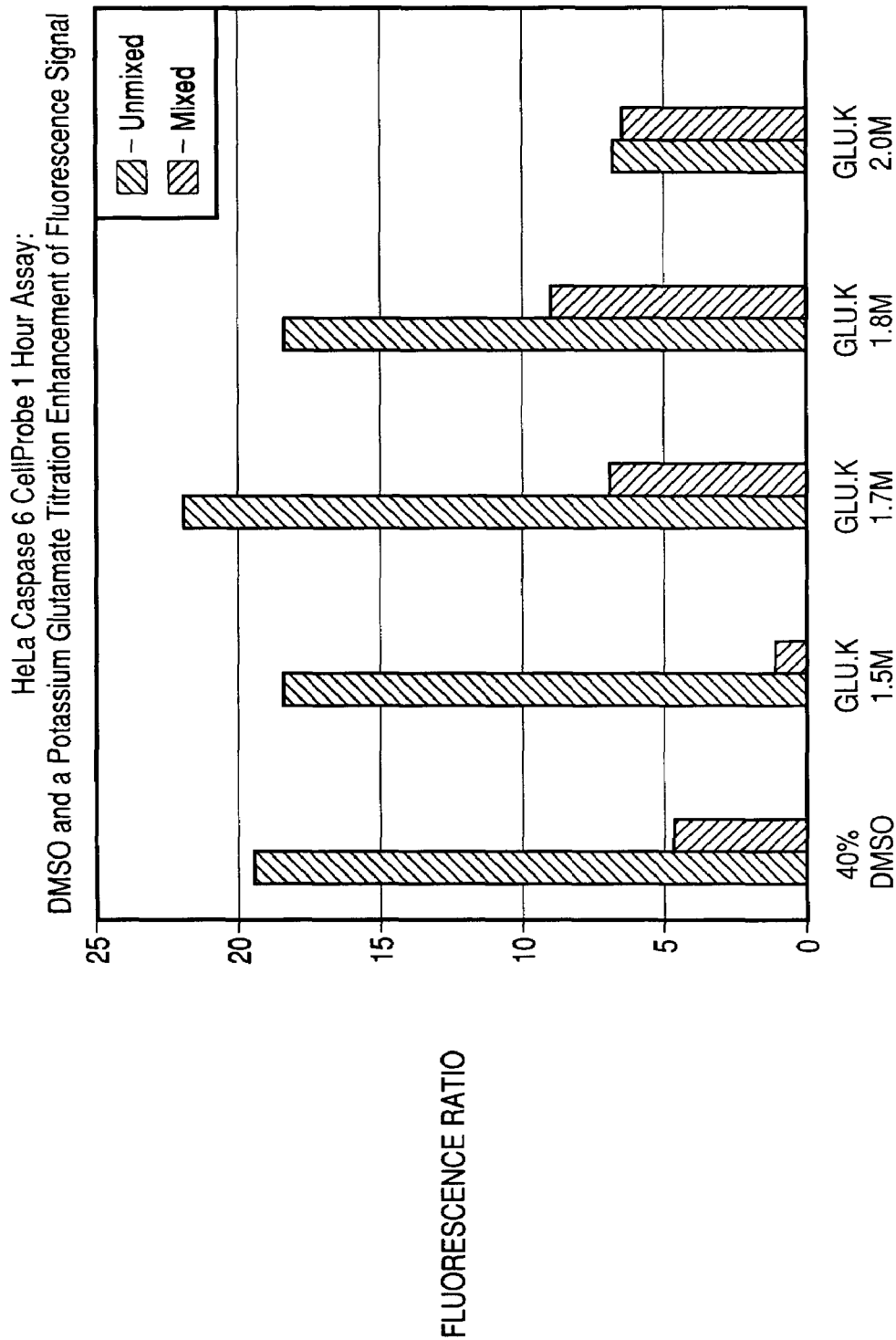
FIG. 5 demonstrates the improved detection of Caspase 6 activity in the presence of glutamate.

As can be seen in FIG. 5, a dramatic improvement in detection of Caspase 6 activity is realized when various concentrations (1.5 M, 1.7 M, 1.8 M, and 2.0 M) of glutamate were employed. In FIG. 5, and in the examples below, the Fluorescence Ratio is defined as:

Fluorescence Ratio=Induced Fluorescence/Uninduced Fluorescence where the Induced Fluorescence is the difference between the 1 Hour Value and the Start of Assay Value, and the Uninduced Fluorescence is the difference between the 1 Hour Value and the Uninduced Start Value. In FIG. 5, data are plotted as a function of potassium glutamate or DMSO concentration. The dark columns indicate results obtained upon mixing the samples, while the light columns indicate results obtained when the samples were not mixed after the addition of glutamate. The data show that inclusion of glutamate (particularly if unmixed) improved assay sensitivity.

EXAMPLE 3

Improved Assay Using Cbz CellProbe™ Reagents

The enhanced detection sensitivity of the assays of the present invention resulting from the use of Cbz-blocked cellprobe reagents (Molecular Probes) is demonstrated by the large increases in signal to noise ratio observed (FIG. 6A). At the lower 10 µM substrate concentrations, 7500 seeded cells and with apparent similar responses to potassium glutamate additions previously observed, it outperforms the unblocked substrate. The data thus show that inclusion of Cbz cellprobe reagents (particularly if unmixed) improved assay sensitivity.

FIG. 6B shows the unprecedented increase in signal level increase of induced caspase 3 detection sensitivity. For the experiment, 7500 HeLa cells/well were plated overnight; Cbz-blocked cellprobe reagents (Molecular Probes) final concentration is 30 µM.

FIG. 6C shows the signal to background ratio ("S/N ratio") of the Cbz-blocked cellprobe reagents (Molecular Probes). The S/N ratio is found to be increased to very high specific values.

EXAMPLE 4

Improved Assay Using Betaine

The enhanced detection sensitivity of the assays of the present invention resulting from the use of betaine is demonstrated by assay results presented in FIG. 7. For such experiments, HeLa cells are seeded overnight at $1.5 \times 10^4$/well and provided with 30 µM CellProbe substrate (final concentration). The data show that inclusion of betaine particularly if unmixed) improved assay sensitivity.

EXAMPLE 5

Improved Assay Using Betaine

Figure 8:
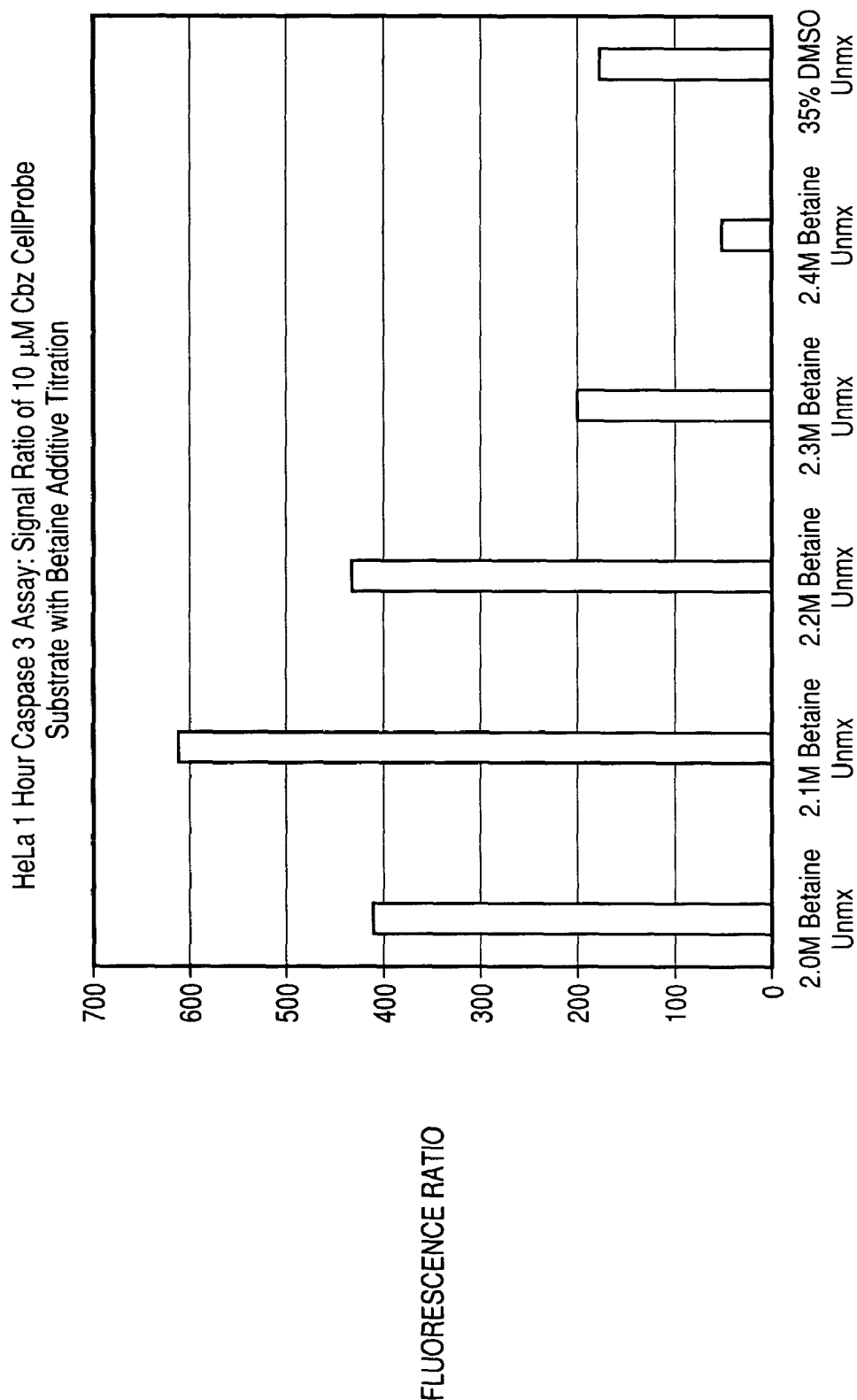
FIG. 8 demonstrates the enhanced detection sensitivity of the assays of the present invention in the presence betaine in combination with DMSO and a Cbz-containing Assay Compound.

The enhanced detection sensitivity of the assays of the present invention resulting from the use of Betaine (at 2.0, 2.1, 2.2, 2.3, 2.4 M) is shown in FIG. 8. For such experiments, HeLa cells are seeded overnight at $7.5 \times 10^3$/well and provided with CellProbe substrate (25 µM final concentration). The data show that inclusion of betaine (particularly if unmixed) improved assay sensitivity. Results of similar assays conducted with 35% DMSO are shown for comparison.

EXAMPLE 6

Improved Assay Using Threitol, Trehalose, Ethylene Glycol, Ribose, and Trimethylamine N-Oxide The enhanced detection sensitivity of the assays of the present invention resulting from the use of threitol, trehalose, ethylene glycol, ribose and trimethylamine N-oxide is demonstrated by assay results of Caspase 6 presented in FIG. 9. To initiate such assays, Caspase CellProbe Reagent™ (Beckman Coulter) is added to a suspension of $1.5 \times 10^4$ HeLa cells/well in a 96-well microtiter plate. The final concentration of the Caspase CellProbe Reagent™ was 30 µM. Reaction is for 1 hour and is as described in Example 1. The data show that inclusion of these agents improved assay performance (results for uninduced samples are shown in dark bars; results for induced samples are shown in lightly shaded bars). The inclusion of glutamic acid diethyl ester or proline did not enhance detection sensitivity.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for assaying a metabolically active whole cell for the presence or activity of an enzyme, comprising the steps:
   (a) providing a sample comprising an intact metabolically active whole cell in medium; and
   (b) providing a mixture composition comprising a substrate of said enzyme or an analyte compound and an agent that enhances/uptake of said substrate or analyte compound; and
   (c) adding said mixture composition to said sample, wherein said mixture composition subsides within said medium of said sample to form a layer of said mixture composition over said intact metabolically active whole cell, wherein said layer is not homogeneously mixed with said medium of said sample; and
   (d) assaying said sample for any change in concentration of said substrate or analyte compound or of a product formed via action of said enzyme on said substrate or analyte, wherein said cell remains intact at the conclusion of said assay, wherein a change in said concentration is indicative of the presence or activity of said enzyme in said metabolically active whole cell; and wherein said agent that enhances uptake of said substrate or analyte is selected from the group consisting of glycerol, dimethyl sulfoxide (DMSO), trehalose, glutamate, betaine, ethylene glycol, threitol, ribose, and trimethylamine N-oxide, with the proviso that when said agent is dimethyl sulfoxide (DMSO), said agent will be present at a concentration of between about 20% and about 60% (v/v).

2. The method of claim 1, wherein said enzyme is selected from the group consisting of a 5' nucleotidase, acetylcholinesterase, an acid phosphatase, an acidic esterase, an acidic esterase I, an acidic esterase II, an acidic non-specific esterase, an adenosine deaminase, an adenosine monophosphate deaminase, an alkaline phosphatase, an aminopeptidase A, an aminopeptidase B, an aminopeptidase M, an aminopentidase N, an angiotensin converting enzyme, a caspase, a cathepsin B, a cathepsin B1, a cathepsin C, a cathepsin D, a cathepsin H, a cathepsin L, a cholinesterase, a chymotrypsin, a collagenase, a cytosine deaminase, a DPP I, a DPP II, a DPP IV, an elastase, an endopeptidase I, an endopeptidase II, an ester proteinase, a galactopyranosidase, a glucoronidase, a glycopyranosidase, a guanine deaminase, an HIV Protease, a lipase, a membrane associated endopeptidase I, a membrane associated endopeptidase II, a neutral endopeptidase, a neutral esterase, a neutral esterase I, a neutral esterase II, a neutral non-specific esterase, a nucleosidase, a pancreatin, a phospholipase A, a phospholipase C, a phospholipase D, a plasmin, a serine phosphatase, a tartrate resistant phosphatase, a tartrate resistant phosphatase, a threonine phosphatase, a thymidine deaminase, a tripeptidyl peptidase, a trypsin, a tyrosine phosphatase, a urokinase, and a γ-glutamyl transpeptidase (γ-GT).

3. The method of claim 2, wherein said enzyme is a caspase.

4. The method of claim 3, wherein said caspase is caspase 1, caspase 3, caspase 6, caspase 8 or caspase 9.

5. The method of claim 1, wherein multiple enzymes are simultaneously assayed.

6. The method of claim 1, wherein multiple enzymes are sequentially assayed.

7. The method of claim 1, wherein said substrate or analyte compound comprises an indicator group and one or more leaving groups, each of said leaving groups being selected for cleavage by said enzyme, said indicator group being in a first state when bonded to a leaving group, and being in a second state when said leaving group is cleaved from said indicator group by said enzyme; and wherein said step (b) comprises sensing whether said second state of said indicator group is produced; wherein the production of said second state of said indicator group is indicative of the presence or activity of said enzyme in said metabolically active whole cell.

8. The method of claim 7, wherein said indicator group is a fluorescent, colorimetric, bioluminescent or chemiluminescent indicator group.

9. The method of claim 7, wherein said uptake-enhancing agent is glycerol.

10. The method of claim 9, wherein said glycerol concentration is between about 5% and about 60% (v/v).

11. The method of claim 10, wherein said glycerol concentration is between about 20% and about 60% (v/v).

12. The method of claim 11, wherein said glycerol concentration is between about 25% and about 40% (v/v).

13. The method of claim 1, wherein said uptake-enhancing agent is dimethyl sulfoxide (DMSO).

14. The method of claim 1, wherein said uptake-enhancing agent is glutamate.

15. The method of claim 14, wherein said glutamate concentration is between about 0.25 M and about 2 M.

16. The method of claim 15, wherein said glutamate concentration is between about 1 M and about 2 M.

17. The method of claim 1, wherein said uptake-enhancing agent is betaine.

18. The method of claim 17, wherein said betaine concentration is about 0.3 M or greater.

19. The method of claim 1, wherein said uptake-enhancing agent is trehalose.

20. The method of claim 19, wherein said trehalose concentration is between about 0.1 M and about 1.5 M.

21. The method of claim 1, wherein said uptake-enhancing agent is ethylene glycol.

22. The method of claim 21, wherein said ethylene glycol concentration is between about 2 M and about 7 M.

23. The method of claim 1, wherein said uptake-enhancing agent is threitol.

24. The method of claim 23, wherein said threitol concentration is between about 1 M and about 5 M.

25. The method of claim 1, wherein said uptake-enhancing agent is ribose.

26. The method of claim 25, wherein said ribose concentration is between about 0.4 M and about 4 M.

27. The method of claim 1, wherein said uptake-enhancing agent is triethylamine N-oxide.

28. The method of claim 27, wherein said triethylamine N-oxide concentration is between about 0.4 M and about 4 M.

29. The method of claim 7, wherein said enzyme is selected from the group consisting of a 5' nucleotidase, acetylcholinesterase, an acid phosphatase, an acidic esterase, an acidic esterase I, an acidic esterase II, an acidic non-specific esterase, an adenosine deaminase, an adenosine monophosphate deaminase, an alkaline phosphatase, an aminopeptidase A, an aminopeptidase B, an aminopeptidase M, an aminopentidase N, an angiotensin converting enzyme, a caspase, a cathepsin B, a cathepsin B1, a cathepsin C, a cathepsin D, a cathepsin H, a cathepsin L, a cholinesterase, a chymotrypsin, a collagenase, a cytosine deaminase, a DPP I, a DPP II, a DPP IV, an elastase, an endopeptidase I, an endopeptidase II, an ester proteinase, a galactopyranosidase, a glucoronidase, a glycopyranosidase, a guanine deaminase, an HIV Protease, a lipase, a membrane associated endopeptidase I, a membrane associated endopeptidase II, a neutral endopeptidase, a neutral esterase, a neutral esterase I, a neutral esterase II, a neutral non-specific esterase, a nucleosidase, a pancreatin, a phospholipase A, a phospholipase C, a phospholipase D, a plasmin, a serine phosphatase, a tartrate resistant phosphatase, a tartrate resistant phosphatase, a threonine phosphatase, a thymidine deaminase, a tripeptidyl peptidase, a trypsin, a tyrosine phosphatase, a urokinase, and a γ-glutamyl transpeptidase (γ-GT).

30. The method of claim 29, wherein said enzyme is a caspase.

31. The method of claim 30, wherein said caspase is caspase 1, caspase 3, caspase 6, caspase 8, or caspase 9.

32. The method of claim 7, wherein multiple enzymes are simultaneously assayed.

33. The method of claim 7, wherein multiple enzymes are sequentially assayed.

34. The method of claim 7, wherein said step (b) includes measuring an intensity of said second state against time.

35. The method of claim 7, wherein said step (b) includes measuring a magnitude of said second state at a point of time.

36. The method of claim 7, wherein said substrate or analyte compound comprises more than one leaving group, and wherein each of said substrate's leaving groups is cleaved sequentially by said enzyme.

37. The method of claim 7, wherein said indicator group is selected from the group consisting of rhodamine 110, rhodol, fluorescein, coumarin, and derivatives thereof.

38. The method of claim 37, wherein said derivatives of rhodamine 110, rhodol, fluorescein and coumarin are selected from the group consisting of 4'(5')thiofluorescein, 4'(5')-aminofluorescein, 4'(5')-carboxyfluorescein, 4'(5')-chlorofluorescein, 4'(5')-methylfluorescein, 4'(5')-sulfofluorescein, 4'(5')-aminorhodol, 4'(5')-carboxyrhodol, 4'(5')-chlororhodol, 4'(5')-methylrhodol, 4'(5')-sulforhodol; 4'(5')-aminorhodamine 110, 4'(5')-sulforhodamine 110, 4'(5') thiorhodamine 110, 7-aminocoumarin, and sulfonated coumarin.

39. The method of claim 7, wherein said assay detects the presence or absence of an abnormality in the activity of said enzyme by comparing the production of said second state of said indicator group by said test cell to the production of said second state of said indicator group by a reference normal cell.

40. The method of claim 39, wherein said abnormality is a morphological or disease state.

41. The method of claim 40, wherein said morphological state is an apoptotic state.

42. The method of claim 40, wherein said disease state is a tumorigenic state.

43. The method of claim 7, wherein said substrate or analyte compound contains a blocking group.

44. The method of claim 43, wherein said blocking group is a Cbz blocking group.

* * * * *